United States Patent
Bissantz et al.

(10) Patent No.: US 8,076,360 B2
(45) Date of Patent: *Dec. 13, 2011

(54) INDOLES

(75) Inventors: Caterina Bissantz, Village-Neuf (FR); Christophe Grundschober, Rodersdorf (CH); Raffaello Masciadri, Basel (CH); Hasane Ratni, Habsheim (FR); Mark Rogers-Evans, Oberwil BL (CH); Patrick Schnider, Bottmingen (CH)

(73) Assignee: Hoffman-La Roche Inc., Nutley, NJ (US)

( * ) Notice: Subject to any disclaimer, the term of this patent is extended or adjusted under 35 U.S.C. 154(b) by 1047 days.

This patent is subject to a terminal disclaimer.

(21) Appl. No.: 11/947,851

(22) Filed: Nov. 30, 2007

(65) Prior Publication Data
US 2008/0139549 A1    Jun. 12, 2008

(30) Foreign Application Priority Data
Dec. 8, 2006    (EP) .................................... 06125666

(51) Int. Cl.
A61K 31/454  (2006.01)
C07D 401/14  (2006.01)

(52) U.S. Cl. ......... 514/323; 514/321; 546/198; 546/201
(58) Field of Classification Search .................. 514/321, 514/323; 546/198, 323, 201
See application file for complete search history.

(56) References Cited

U.S. PATENT DOCUMENTS

| 7,799,923 B2 * | 9/2010 | Bissantz et al. | 546/199 |
| 2008/0139617 A1 * | 6/2008 | Bissantz et al. | 514/321 |

FOREIGN PATENT DOCUMENTS

| WO | WO 00/14067 | 3/2000 |
| WO | WO 01/85725 | 11/2001 |
| WO | WO 02/34718 | 5/2002 |
| WO | WO 2004/035549 | 4/2004 |
| WO | WO 2005/005411 | 1/2005 |

OTHER PUBLICATIONS

Bottcher et al. "Preparation of benzyl . . . " CA 130:81409 (1999).*
Ebner et al., (2002), Eur. J. Neurosci. vol. 15 pp. 384-388.
Bielsky et al., (2004), Neuropsychopharmacology, vol. 29 pp. 483-493.
Michelini et al., (1999), Annals NY Acad. Sci. vol. 897 pp. 198-211.
Van Kerckhoven et al., (2002) Eur. J. Pharmacol. vol. 449 pp. 135-141.
Liebsch et al., (1995), Regulatory Peptides vol. 59 pp. 229-239.

* cited by examiner

Primary Examiner — Celia Chang
(74) Attorney, Agent, or Firm — George W. Johnston; Patricia S. Rocha-Tramaloni; Kimberly J. Prior

(57) ABSTRACT

The present invention is concerned with novel indol-2-yl-carbonyl-piperidine derivatives as V1a receptor antagonists, their manufacture, pharmaceutical compositions containing them and their use as medicaments. The active compounds of the present invention are useful in the prevention and/or treatment of anxiety and depressive disorders and other diseases. Present invention is concerned with compounds of the general formula (I)

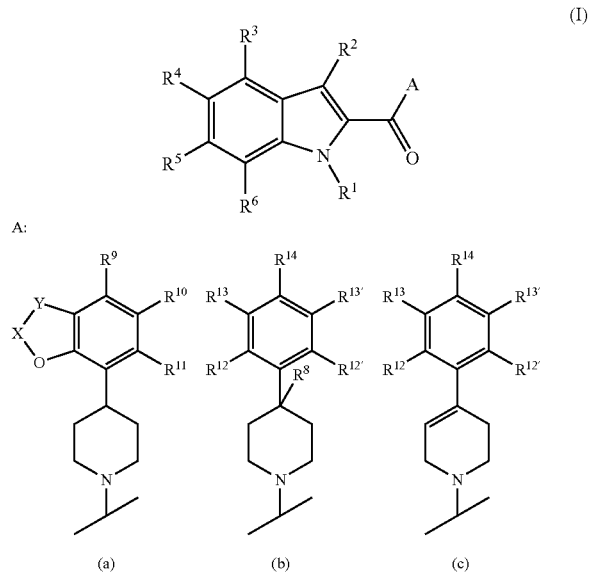

wherein $R^1$ to $R^6$, $R^8$ to $R^{14}$, $R^{12'}$, $R^{13'}$, X and Y are as defined in the specification.

18 Claims, No Drawings

INDOLES

PRIORITY TO RELATED APPLICATION(S)

This application claims the benefit of European Patent Application No. 06125666.5, filed Dec. 8, 2006, which is hereby incorporated by reference in its entirety.

BACKGROUND OF THE INVENTION

Vasopressin is a 9 amino acid peptide mainly produced by the paraventricular nucleus of the hypothalamus. Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water excretion and mediates the antidiuretic effects of vasopressin.

In the periphery vasopressin acts as a neurohormone and stimulates vasoconstriction, glycogenolysis and antidiuresis. In the brain vasopressin acts as a neuromodulator and is elevated in the amygdala during stress (Ebner, K., C. T. Wotjak, et al. (2002). "Forced swimming triggers vasopressin release within the amygdala to modulate stress-coping strategies in rats." *Eur J Neurosci* 15(2): 384-8). The V1a receptor is extensively expressed in the brain and particularly in limbic areas like the amygdala, lateral septum and hippocampus which are playing an important role in the regulation of anxiety. Indeed V1a knock-out mouse show a reduction in anxious behavior in the plus-maze, open field and light-dark box (Bielsky, I. F., S. B. Hu, et al. (2003). "Profound Impairment in Social Recognition and Reduction in Anxiety-Like Behavior in Vasopressin V1a Receptor Knockout Mice." *Neuropsychopharmacology*). The downregulation of the V1a receptor using antisense oligonucleotide injection in the septum also causes a reduction in anxious behavior (Landgraf, R., R. Gerstberger, et al. (1995). "V1 vasopressin receptor antisense oligodeoxynucleotide into septum reduces vasopressin binding, social discrimination abilities, and anxiety-related behavior in rats." *Regul Pept* 59(2): 229-39).

The V1a receptor is also mediating the cardiovascular effects of vasopressin in the brain by centrally regulating blood pressure and heart rate in the solitary tract nucleus (Michelini, L. C. and M. Morris (1999). "Endogenous vasopressin modulates the cardiovascular responses to exercise." *Ann NY Acad Sci* 897: 198-211). In the periphery it induces the contraction of vascular smooth muscles and chronic inhibition of the V1a receptor improves hemodynamic parameters in myocardial infarcted rats (Van Kerckhoven, R., I. Lankhuizen, et al. (2002). "Chronic vasopressin V(1A) but not V(2) receptor antagonism prevents heart failure in chronically infarcted rats." *Eur J Pharmacol* 449(1-2): 135-41).

SUMMARY OF THE INVENTION

The present invention provides novel indol-2-yl-carbonyl-piperidine derivatives as V1a receptor antagonists, their manufacture, pharmaceutical compositions containing them and their use for the treatment of anxiety and depressive disorders and other diseases.

In particular, the present invention provides compounds of formula (I)

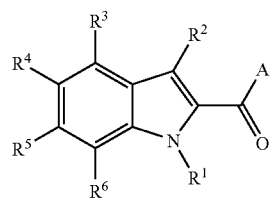

(I)

wherein A is

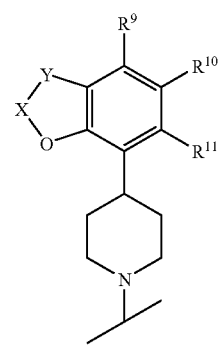

(a)

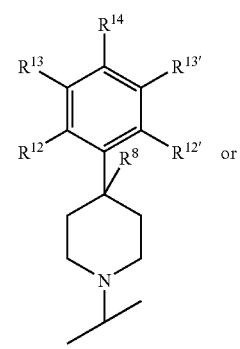

(b) or

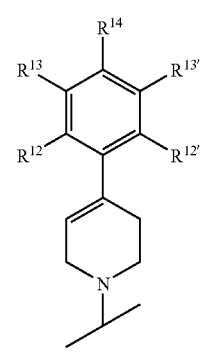

(c)

X is C=O and Y is $NR^7$, or
X is $CH_2$ and Y is O, or
X is $CH_2$ and Y is $CH_2$;
$R^1$ is hydrogen,
  $C_{1-6}$-alkyl, optionally substituted by CN or OH, or
  —($C_{1-6}$-alkylene)-C(O)—$NR^aR^b$;

$R^2$ is hydrogen,
  $C_{1-6}$-alkyl,
  $C_{1-6}$-alkoxy,
  —($C_{1-6}$-alkylene)-$NR^cR^d$,
  —($C_{1-6}$-alkylene)-$C(O)R^f$,
    benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or
    phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
$R^3$ is hydrogen,
  halo, or
  $C_{1-6}$-alkyl;
$R^4$ is hydrogen,
  halo,
  $C_{1-6}$-alkyl,
  halo-$C_{1-6}$-alkyl,
  $C_{1-6}$-alkoxy,
  halo-$C_{1-6}$-alkoxy, or
  —O—$C_{2-10}$-alkenyl;
$R^5$ is hydrogen,
  halo,
  $C_{1-6}$-alkyl, or
  $C_{1-6}$-alkoxy;
or $R^4$ and $R^5$ are bound together to form a ring with the benzo moiety, wherein
  —$R^4$—$R^5$— is —O—$(CH_2)_n$—O— wherein n is 1 or 2;
$R^6$ is hydrogen,
  $C_{1-6}$-alkyl, optionally substituted by CN or OH,
  —($C_{1-6}$-alkylene)-$NR^gR^h$
  —($C_{1-6}$-alkylene)-C(O)—$NR^iR^j$
  —O-benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
  nitro,
  halo,
  cyano,
  $C_{1-6}$-alkoxy,
  halo-$C_{1-6}$-alkoxy,
  halo-$C_{1-6}$-alkyl,
  —($C_{1-6}$-alkylene)-$C(O)R^f$,
  phenyl, or 5 to 6-membered heteroaryl, optionally substituted by halo, halo-$C_{1-6}$-alkyl, $C_{1-6}$-alkyl, $C_{1-6}$-alkoxy, halo-$C_{1-6}$-alkoxy, nitro, or cyano, or
  —($C_{1-3}$-alkylene)-$R^m$, wherein $R^m$ is phenyl, a 5- to 6-membered heteroaryl, 4- to 6-membered heterocycloalkyl or 3 to 6-membered cycloalkyl,
    each optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
or $R^5$ and $R^6$ are bound together to form a ring with the benzo moiety, wherein
  —$R^5$—$R^6$ is —O—$(CH_2)_n$—C(O)—,
  —C(O)—$(CH_2)$, —O—, or
  —O—$(CH_2)$, —O— wherein n is 1 or 2;
$R^7$ is hydrogen or $C_{1-6}$-alkyl;
$R^8$ is hydrogen,
  $C_{1-6}$-alkoxy,
  CN,
  OH,
  $COOR^n$, or
  $C(O)NR^oR^p$;
$R^9$, $R^{10}$, and $R^{11}$ are each independently hydrogen, halo, $C_{1-6}$-alkyl, halo-$C_{1-6}$-alkyl, $C_{1-6}$-alkoxy or halo-$C_{1-6}$-alkoxy;

$R^{12}$, $R^{12'}$, $R^{13}$, $R^{13'}$, and $R^{14}$ are each independently hydrogen, $C_{1-6}$-alkoxy, $C_{1-6}$-alkyl, halo, halo-$C_{1-6}$-alkoxy, halo-$C_{1-6}$-alkyl, or nitro;
$R^a$, $R^b$, $R^i$ and $R^j$ are each independently
  hydrogen,
  $C_{1-6}$-alkyl,
  —($C_{1-6}$-alkylene)-$NR^kR^l$,
    wherein $R^k$ and $R^l$ are each independently hydrogen or $C_{1-6}$-alkyl,
  or
  $R^a$ and $R^b$, or $R^i$ and $R^j$ together with the nitrogen to which they are bound form a five or six membered heterocycle comprising one or two heteroatoms selected from the group consisting of nitrogen, oxygen and sulfur;
$R^c$, $R^d$, $R^g$ and $R^h$ are each independently
  hydrogen,
  $C_{1-6}$-alkyl,
  —$C(O)R^e$, or —$S(O)_2R^e$,
    wherein $R^e$ is selected from
      hydrogen,
      $C_{1-6}$-alkyl, or
      phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or
  $R^c$ and $R^d$, or $R^g$ and $R^h$ together with the nitrogen to which they are bound form a five or six membered heterocycle comprising one or two heteroatoms selected from the group consisting of nitrogen, oxygen and sulfur, or
  $R^c$ and $R^d$, or $R^g$ and $R^h$ together with the nitrogen to which they are bound form isoindole-1,3-dione;
$R^f$ is selected from the group consisting of
  hydrogen,
  $C_{1-6}$-alkyl,
  $C_{1-6}$-alkoxy, or
  phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
$R^n$, $R^o$ and $R^p$ are each independently selected from the group consisting of hydrogen and $C_{1-6}$-alkyl,
as well as pharmaceutically acceptable salts thereof.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The compounds of formula (I) possess pharmaceutical activity, in particular they are modulators of V1a receptor activity. More particular, the compounds are antagonists of the V1a receptor. The invention provides methods for the treatment of dysmenorrhea, hypertension, chronic heart failure, inappropriate secretion of vasopressin, liver cirrhosis, nephrotic syndrome, obsessive compulsive disorder, anxiety and depressive disorders. The preferred indications with regard to the present invention are the treatment of anxiety and depressive disorders.

DETAILED DESCRIPTION OF INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

In the present description, the term "alkyl", alone or in combination with other groups, refers to a branched or straight-chain monovalent saturated hydrocarbon radical. In particular, the term "$C_{1-6}$-alkyl" denotes a saturated straight- or branched-chain monovalent hydrocarbon group containing from 1 to 6 carbon atoms, for example, methyl, ethyl, n-propyl, isopropyl, n-butyl, isobutyl, tert-butyl, the isomeric pentyls and the like. A preferred sub-group of $C_{1-6}$-alkyl is $C_{1-4}$-alkyl, i.e. with 1-4 carbon atoms.

In the present invention, the term "alkylene" refers to a linear or branched saturated divalent hydrocarbon radical. In particular, "$C_{1-6}$-alkylene" means a linear saturated divalent hydrocarbon radical of one to six carbon atoms or a branched saturated divalent hydrocarbon radical of three to six carbon atoms, e.g. methylene, ethylene, 2,2-dimethylethylene, n-propylene, 2-methylpropylene, and the like.

In the present description, the terms "alkoxy" and "$C_{1-6}$-alkoxy" refer to the group R'—O—, wherein R' is $C_{1-6}$-alkyl as defined above. Examples of alkoxy groups are methoxy, ethoxy, n-propoxy, isopropoxy, n-butoxy, tert-butoxy, sec-butoxy and the like. A preferred sub-group of $C_{1-6}$-alkoxy, and still more preferred alkoxy groups are methoxy and/or ethoxy.

In the present description, the terms "thioalkyl" and "$C_{1-6}$-thioalkyl" refer to the group R'—S—, wherein R' is $C_{1-6}$-alkyl as defined above.

The terms "$C_{1-6}$-hydroxyalkyl" and "$C_{1-6}$-alkyl substituted by OH" denote a $C_{1-6}$-alkyl group as defined above wherein at least one of the hydrogen atoms of the alkyl group is replaced by a hydroxyl group.

The terms "$C_{1-6}$-cyanoalkyl" and "$C_{1-6}$-alkyl substituted by CN" denote a $C_{1-6}$-alkyl group as defined above wherein at least one of the hydrogen atoms of the alkyl group is replaced by a CN group.

The terms "halo" or "halogen" refer to fluorine (F), chlorine (Cl), bromine (Br) and iodine (I) with fluorine, chlorine and bromine being preferred.

The term "halo-$C_{1-6}$-alkyl" denotes a $C_{1-6}$-alkyl group as defined above wherein at least one of the hydrogen atoms of the alkyl group is replaced by a halogen atom, preferably fluoro or chloro, most preferably fluoro. Examples of halo-$C_{1-6}$-alkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below.

Among the preferred halo-$C_{1-6}$-alkyl groups are difluoro- or trifluoro-methyl or -ethyl.

The term "halo-$C_{1-6}$-alkoxy" denotes a $C_{1-6}$-alkoxy group as defined above wherein at least one of the hydrogen atoms of the alkyl group is replaced by a halogen atom, preferably fluoro or chloro, most preferably fluoro. Among the preferred halogenated alkoxy groups are difluoro- or trifluoro-methoxy or -ethoxy.

The term "$C_{2-12}$-alkenyl", alone or in combination, denotes a straight-chain or branched hydrocarbon residue of 2 to 12 carbon atoms comprising at least one double bond. A preferred sub-group of $C_{2-12}$-alkenyl is $C_{2-6}$-alkyenyl. Examples of the preferred alkenyl groups are ethenyl, propen-1-yl, propen-2-yl(allyl), buten-1-yl, buten-2-yl, buten-3-yl, penten-1-yl, penten-2-yl, penten-3-yl, penten-4-yl, hexen-1-yl, hexen-2-yl, hexen-3-yl, hexen-4-yl and hexen-5-yl, as well as those specifically illustrated by the examples herein below.

The term "5 or 6 membered heteroaryl" means an aromatic ring of 5 or 6 ring atoms as ring members containing one, two, or three ring heteroatoms selected from N, O, and S, the rest being carbon atoms. 5 or 6 membered heteroaryl can optionally be substituted with one, two, three or four substituents, wherein each substituent are independently selected from the group consisting of hydroxy, $C_{1-6}$-alkyl, $C_{1-6}$-alkoxy, $C_{1-6}$-thioalkyl, halo, cyano, nitro, halo-$C_{1-6}$-alkyl, $C_{1-6}$-hydroxyalkyl, $C_{1-6}$-alkoxycarbonyl, amino, $C_{1-6}$-alkylamino, di($C_{1-6}$)alkylamino, aminocarbonyl, and carbonylamino, unless otherwise specifically indicated. Preferred substituents are halo, halo-$C_{1-6}$-alkyl, $C_{1-6}$-alkyl, $C_{1-6}$-alkoxy, halo-$C_{1-6}$-alkoxy, nitro, or cyano. Examples of heteroaryl moieties include, but are not limited to, optionally substituted imidazolyl, optionally substituted oxazolyl, optionally substituted thiazolyl, optionally substituted pyrazinyl, optionally substituted pyrrolyl, optionally substituted pyrazinyl, optionally substituted pyridinyl, optionally substituted pyrimidinyl, optionally substituted furanyl, and those which are specifically exemplified herein.

The term "heterocycloalkyl" means a monovalent saturated moiety, consisting of one ring of 3 to 7, preferably from 4 to 6 atoms as ring members, including one, two, or three heteroatoms chosen from nitrogen, oxygen and sulfur, the rest being carbon atoms. 3 to 7 membered heterocycloalkyl can optionally be substituted with one, two, three or four substituents, wherein each substituent is independently hydroxy, $C_{1-6}$-alkyl, $C_{1-6}$-alkoxy, $C_{1-6}$-thioalkyl, halo, cyano, nitro, halo-$C_{1-16}$-alkyl, $C_{1-6}$-hydroxyalkyl, $C_{1-6}$-alkoxycarbonyl, amino, $C_{1-6}$-alkylamino, di($C_{1-6}$)alkylamino, aminocarbonyl, or carbonylamino, unless otherwise specifically indicated. Preferred substituents are halo, halo-$C_{1-6}$-alkyl, $C_{1-6}$-alkyl, $C_{1-6}$-alkoxy, halo-$C_{1-6}$-alkoxy, nitro, or cyano. Examples of heterocyclic moieties include, but are not limited to, optionally substituted tetrahydro-furanyl, optionally substituted piperidinyl, optionally substituted pyrrolidinyl, optionally substituted morpholinyl, optionally substituted piperazinyl, and the like or those which are specifically exemplified herein.

The term "heterocycle" in the definition "$R^a$ and $R^b$, $R^c$ and $R^d$, $R^g$ and $R^h$, $R^i$ and $R^j$, together with the nitrogen to which they are bound form a five- or six-membered heterocycle comprising one or two heteroatoms selected from the group consisting of nitrogen, oxygen and sulfur" means either heterocycloalkyl or heteroaryl in the above-given sense which may optionally be substituted as described above. Preferably, the "heterocycle" may optionally be substituted with one, two or three substituents selected from halo, halo-$C_{1-6}$-alkyl, $C_{1-6}$-alkyl, $C_{1-6}$-alkoxy, halo-$C_{1-6}$-alkoxy, nitro, and cyano. Preferred heterocycles are piperazine, N-methylpiperazine, morpholine, piperidine and pyrrolidine.

The term "one or more" substituents preferably means one, two or three substituents per ring.

The term "cycloalkyl" means a cycloalkyl group containing 3 to 6, carbon atoms, such as cyclopropyl, cyclobutyl, cyclopentyl or cyclohexyl. Cycloalkyl containing 3 to 4 carbon atoms are the most preferred.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

In detail, the present invention provides compounds of formula (I)

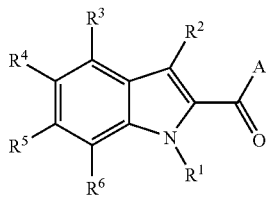

(I)

wherein A is

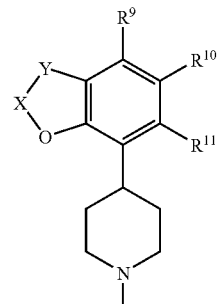

(a)

or

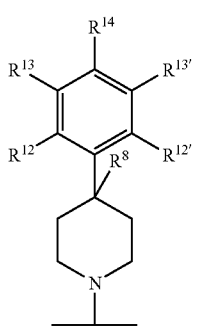

(b)

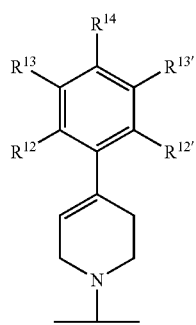

(c)

X is C=O and Y is $NR^7$, or
X is $CH_2$ and Y is O, or
X is $CH_2$ and Y is $CH_2$,
$R^1$ is hydrogen,
  $C_{1-6}$-alkyl, optionally substituted by CN or OH, or
  —($C_{1-6}$-alkylene), —C(O)—$NR^aR^b$;

$R^2$ is hydrogen,
  $C_{1-6}$-alkyl,
  $C_{1-6}$-alkoxy,
  —($C_{1-6}$-alkylene)-$NR^cR^d$,
  —($C_{1-6}$-alkylene)-$C(O)R^f$,
  benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or
  phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
$R^3$ is hydrogen,
  halo, or
  $C_{1-6}$-alkyl;
$R^4$ is hydrogen,
  halo,
  $C_{1-6}$-alkyl,
  halo-$C_{1-6}$-alkyl,
  $C_{1-6}$-alkoxy,
  halo-$C_{1-6}$-alkoxy, or
  —O—$C_{2-10}$-alkenyl;
$R^5$ is hydrogen,
  halo,
  $C_{1-6}$-alkyl, or
  $C_{1-6}$-alkoxy;
or $R^4$ and $R^5$ are bound together to form a ring with the benzo moiety, wherein
  —$R^4$—$R^5$— is —O—$(CH_2)_n$—O— wherein n is 1 or 2;
$R^6$ is hydrogen,
  $C_{1-6}$-alkyl, optionally substituted by CN or OH,
  —($C_{1-6}$-alkylene)-$NR^gR^h$
  —($C_{1-6}$-alkylene)-C(O)—$NR^iR^j$
  —O-benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
  nitro,
  halo,
  cyano,
  $C_{1-6}$-alkoxy,
  halo-$C_{1-6}$-alkoxy,
  halo-$C_{1-6}$-alkyl,
  —($C_{1-6}$-alkylene)-$C(O)R^f$,
  phenyl, or 5 to 6-membered heteroaryl, optionally substituted by halo, halo-$C_{1-6}$-alkyl, $C_{1-6}$-alkyl, $C_{1-6}$-alkoxy, halo-$C_{1-6}$-alkoxy, nitro, or cyano,
  —($C_{1-3}$-alkylene)-$R^m$, wherein $R^m$ is phenyl, a 5- to 6-membered heteroaryl, 4- to 6-membered heterocycloalkyl or 3 to 6-membered cycloalkyl,
    each optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
or $R^5$ and $R^6$ are bound together to form a ring with the benzo moiety, wherein
  —$R^5$—$R^6$ is —O—$(CH_2)$,—C(O)—,
  —C(O)—$(CH_2)$, —O—, or
  —O—$(CH_2)$, —O— wherein n is 1 or 2;
$R^7$ is hydrogen or $C_{1-6}$-alkyl;
$R^8$ is hydrogen,
  $C_{1-6}$-alkoxy,
  CN,
  OH,
  $COOR^n$, or
  $C(O)NR^oR^p$;
$R^9$, $R^{10}$, and $R^{11}$ are each independently hydrogen, halo, $C_{1-6}$-alkyl, halo-$C_{1-6}$-alkyl, $C_{1-6}$-alkoxy or halo-$C_{1-6}$-alkoxy;

$R^{12}$, $R^{12'}$, $R^{13}$, $R^{13'}$, and $R^{14}$ are each independently hydrogen, $C_{1-6}$-alkoxy, $C_{1-6}$-alkyl, halo, halo-$C_{1-6}$-alkoxy, halo-$C_{1-6}$-alkyl, or nitro;

$R^a$, $R^b$, $R^i$ and $R^j$ are each independently
  hydrogen,
  $C_{1-6}$-alkyl,
  —($C_{1-6}$-alkylene)-$NR^kR^l$,
    wherein $R^k$ and $R^l$ are each independently hydrogen or $C_{1-6}$-alkyl,
  or
  $R^a$ and $R^b$, or $R^i$ and $R^j$ together with the nitrogen to which they are bound form a five or six membered heterocycle comprising one or two heteroatoms selected from the group consisting of nitrogen, oxygen and sulfur;

$R^c$, $R^d$, $R^i$ and $R^j$ are each independently
  hydrogen,
  $C_{1-6}$-alkyl,
  —C(O)$R^e$, or —S(O)$_2R^e$,
    wherein $R^e$ is selected from
      hydrogen,
      $C_{1-6}$-alkyl, and
      phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or
  $R^c$ and $R^d$, or $R^g$ and $R^h$ together with the nitrogen to which they are bound form a five or six membered heterocycle comprising one or two heteroatoms selected from the group consisting of nitrogen, oxygen and sulfur, or
  $R^c$ and $R^d$, or $R^g$ and $R^h$ together with the nitrogen to which they are bound form isoindole-1,3-dione;

$R^f$ is selected from
  hydrogen,
  $C_{1-6}$-alkyl,
  $C_{1-6}$-alkoxy, and
  phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;

$R^n$, $R^o$ and $R^p$ are each independently selected from the group consisting of hydrogen and $C_{1-6}$-alkyl, as well as pharmaceutically acceptable salts thereof.

In certain embodiments of the invention, $R^a$ and $R^b$, $R^c$ and $R^d$, $R^i$ and $R^j$, or $R^g$ and $R^h$ together with the nitrogen to which they are bound may form piperazine, 4-($C_{1-6}$-alkyl)-piperazine, 4-methylpiperazine, morpholine, piperidine or pyrrolidine.

In certain embodiments of the invention, $R^a$ and $R^b$, $R^c$ and $R^d$, $R^i$ and $R^j$, or $R^g$ and $R^h$ together with the nitrogen to which they are bound may form 4-methylpiperazine, or morpholine.

In certain embodiments of the invention, wherein $R^m$ is a 5- to 6-membered heteroaryl, the preferred heteroaryl is selected from the group consisting of pyridine, pyrimidine, pyrazine, pyridazine, imidazole, pyrazole, oxazole, and isoxazole.

In embodiments of the invention, wherein $R^m$ is a 4- to 6-membered heterocycloalkyl, the preferred heterocycloalkyl is selected from the group consisting of pyrrolidine, oxethane, tetrahydropyrane, piperidine, morpholine, and piperazine.

Preferably, compounds of formula (I) according to the invention are those wherein $R^1$, $R^2$, $R^3$, $R^2$, $R^3$ and $R^6$ are not all hydrogen at the same time.

In certain embodiments of the invention, $R^{12}$ and $R^{12'}$ are each independently hydrogen, $C_{1-6}$-alkoxy, $C_{1-6}$-alkyl, halo, halo-$C_{1-6}$-alkoxy, halo-$C_{1-6}$-alkyl, or nitro; $R^{13}$, $R^{13'}$, and $R^{14}$ are each independently hydrogen, $C_{1-6}$-alkoxy, $C_{1-6}$-alkyl, halo, halo-$C_{1-6}$-alkoxy, or nitro.

In certain embodiments of the invention,
$R^1$ is hydrogen,
  $C_{1-6}$-alkyl, optionally substituted by CN or OH, or
  —($C_{1-6}$-alkylene)-C(O)—$NR^aR^b$,
    wherein $R^a$ and $R^b$ are each independently hydrogen or $C_{1-6}$-alkyl.

In certain embodiments of the invention,
$R^2$ is hydrogen,
  $C_{1-6}$-alkyl,
  $C_{1-6}$-alkoxy,
  —($C_{1-6}$-alkylene)-$NR^cR^d$,
    wherein $R^c$ and $R^d$ are each independently
      hydrogen,
      —C(O)$R^e$, or —S(O)$_2R^e$
        wherein $R^e$ is selected from
          hydrogen,
          $C_{1-6}$-alkyl, and
          phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or
      $R^c$ and $R^d$ together with the nitrogen to which they are bound form isoindole-1,3-dione,
  ($C_{1-6}$-alkylene)-C(O)$R^f$,
    wherein $R^f$ is selected from
      hydrogen,
      $C_{1-6}$-alkyl,
      $C_{1-6}$-alkoxy, and
      phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
  benzyl, optionally substituted by halo, halo-$C_{1-6}$-alkyl, $C_{1-6}$-alkyl, $C_{1-6}$-alkoxy, halo-$C_{1-6}$-alkoxy, nitro, or cyano, or
  phenyl, optionally substituted by halo, halo-$C_{1-6}$-alkyl, $C_{1-6}$-alkyl, $C_{1-6}$-alkoxy, halo-$C_{1-6}$-alkoxy, nitro, or cyano.

In certain embodiments of the invention, $R^2$ is hydrogen, or $C_{1-6}$-alkyl.

In certain embodiments of the invention, $R^3$ is hydrogen.

In certain embodiments of the invention, $R^4$ is hydrogen, halo, $C_{1-6}$-alkyl, halo-$C_{1-6}$-alkyl or $C_{1-6}$-alkoxy, preferably, $R^4$ is hydrogen or halo, more preferably, $R^4$ is hydrogen or chloro.

In certain embodiments, $R^5$ is hydrogen, halo, $C_{1-6}$-alkyl, halo-$C_{1-6}$-alkyl or $C_{1-6}$-alkoxy; preferably, $R^5$ is hydrogen.

In certain embodiments of the invention,
$R^6$ is hydrogen,
  $C_{1-6}$-alkyl, optionally substituted by CN or OH,
  —($C_{1-6}$-alkylene)-$NR^gR^h$
    wherein $R^g$ and $R^h$ are each independently selected from hydrogen and $C_{1-6}$-alkyl, or wherein
    $R^g$ and $R^h$ together with the nitrogen to which they are bound form a five or six membered heterocycle comprising one or two heteroatoms selected from the group consisting of nitrogen, oxygen and sulfur,
  —($C_{1-6}$-alkylene)-C(O)—$NR^iR^j$
    wherein $R^i$ and $R^j$ are each independently
      hydrogen,
      $C_{1-6}$-alkyl, or
      —($C_{1-6}$-alkylene)-$NR^kR^l$,
        wherein $R^k$ and $R^l$ are each independently hydrogen or $C_{1-6}$-alkyl,
    or $R^i$ and $R^j$ together with the nitrogen to which they are bound form a five or six membered heterocycle comprising one or two heteroatoms selected from the group consisting of nitrogen, oxygen and sulfur, —O-benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, nitro, halo, cyano, $C_{1-6}$-alkoxy, halo-$C_{1-6}$-alkoxy, halo-$C_{1-6}$-alkyl, —($C_{1-6}$-alkylene)-C(O)$R^f$, $R^f$ is selected from hydrogen, $C_{1-6}$-alkyl, $C_{1-6}$-alkoxy, and phenyl or 5- to 6-membered heteroaryl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, —($C_{1-3}$-alkylene)-$R^m$, wherein $R^m$ is phenyl, a 5- to 6-membered heteroaryl, 4- to 6-membered heterocycloalkyl or 3 to 6-membered cycloalkyl, each optionally substituted by one or more halo, halo-$C_{1-6}$-alkyl, $C_{1-6}$-alkyl, $C_{1-6}$-alkoxy, halo-$C_{1-6}$-alkoxy, nitro, or cyano.

In certain embodiments of the invention, $R^6$ is hydrogen, $C_{1-6}$-alkyl, optionally substituted by CN or OH, —($C_{1-6}$-alkylene)-$NR^gR^h$ wherein $R^g$ and $R^h$ are each independently selected from hydrogen and $C_{1-6}$-alkyl, or wherein $R^g$ and $R^h$ together with the nitrogen to which they are bound form a five or six membered heterocycle comprising one or two heteroatoms selected from the group consisting of nitrogen and oxygen, —($C_{1-6}$-alkylene)-C(O)—$NR^iR^j$ wherein $R^i$ and $R^j$ are each independently hydrogen, $C_{1-6}$-alkyl, or —($C_{1-6}$-alkylene)-$NR^kR^l$, wherein $R^k$ and $R^l$ are each independently hydrogen or $C_{1-6}$-alkyl, or $R^i$ and $R^j$ together with the nitrogen to which they are bound form a five or six membered heterocycle comprising one or two heteroatoms selected from the group consisting of nitrogen and oxygen —($C_{1-3}$-alkylene)-$R^m$, wherein $R^m$ is phenyl, a 5- to 6-membered heteroaryl, 4- to 6-membered heterocycloalkyl or 3 to 6-membered cycloalkyl, each optionally substituted by one or more halo, halo-$C_{1-6}$-alkyl, $C_{1-6}$-alkyl, $C_{1-6}$-alkoxy, halo-$C_{1-6}$-alkoxy, nitro, or cyano.

In certain embodiments of the invention, $R^6$ is hydrogen, $C_{1-6}$-alkyl, optionally substituted by CN, —($C_{1-6}$-alkylene)-$NR^gR^h$ wherein $R^g$ and $R^h$ are each independently selected from hydrogen and $C_{1-6}$-alkyl, or wherein $R^g$ and $R^h$ together with the nitrogen to which they are bound form a five or six membered heterocycle comprising one or two heteroatoms selected from the group consisting of nitrogen and oxygen, —($C_{1-6}$-alkylene)-C(O)—$NR^iR^j$ wherein $R^i$ and $R^j$ are each independently hydrogen, or $C_{1-6}$-alkyl.

In certain embodiments of the invention,

A is (a);

X is C=O and Y is $NR^7$; or

X is $CH_2$ and Y is O, or

X is $CH_2$ and Y is $CH_2$, $R^1$ is hydrogen, $C_{1-6}$-alkyl, optionally substituted by CN or OH, or —($C_{1-6}$-alkylene)-C(O)—$NR^aR^b$, wherein $R^a$ and $R^b$ are each independently hydrogen or $C_{1-6}$-alkyl;

$R^2$ is hydrogen, or $C_{1-6}$-alkyl;

$R^3$ is hydrogen, halo or $C_{1-6}$-alkyl;

$R^4$ is hydrogen, halo, $C_{1-6}$-alkyl, halo-$C_{1-6}$-alkyl, $C_{1-6}$-alkoxy, or halo-$C_{1-6}$-alkoxy;

$R^5$ is hydrogen, halo, $C_{1-6}$-alkyl, or $C_{1-6}$-alkoxy;

or $R^4$ and $R^5$ are bound together to form a ring with the benzo moiety, wherein —$R^4$—$R^5$— is —O—$(CH_2)_n$—O— wherein n is 1 or 2;

$R^6$ is hydrogen, $C_{1-6}$-alkyl, optionally substituted by CN or OH,

—($C_{1-6}$-alkylene)-$NR^gR^h$ wherein $R^g$ and $R^h$ are each independently selected from hydrogen and $C_{1-6}$-alkyl, or wherein $R^g$ and $R^h$ together with the nitrogen to which they are bound form a five or six membered heterocycle comprising one or two heteroatoms selected from the group consisting of nitrogen and oxygen, —($C_{1-6}$-alkylene)-C(O)—$NR^iR^j$ wherein $R^i$ and $R^j$ are each independently hydrogen, $C_{1-6}$-alkyl, —($C_{1-6}$-alkylene)-$NR^kR^l$, wherein $R^k$ and $R^l$ are each independently hydrogen or $C_{1-6}$-alkyl, or $R^i$ and $R^j$ together with the nitrogen to which they are bound form a five or six membered heterocycle comprising one or two heteroatoms selected from the group consisting of nitrogen and oxygen;

$R^7$ is hydrogen or $C_{1-6}$-alkyl;

$R^9$, $R^{10}$, and $R^{11}$ are each independently hydrogen, halo, $C_{1-6}$-alkyl, halo-$C_{1-6}$-alkyl, $C_{1-6}$-alkoxy or halo-$C_{1-6}$-alkoxy.

Preferably, in the above embodiment, where A is (a), X is C=O and Y is NR⁷, i.e. a compound of formula (I-a'):

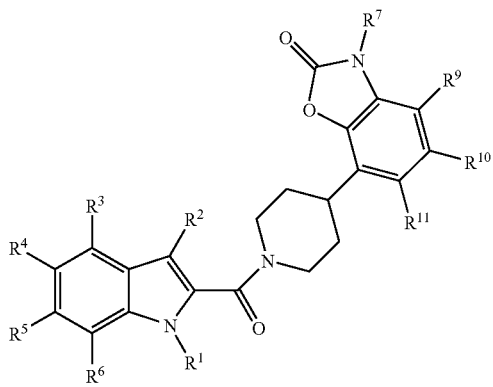

(I-a')

wherein $R^1$ to $R^{11}$ are as defined herein above.

In a certain embodiment, A is (a), X is CH₂ and Y is O, i.e. a compound of formula (I-a″):

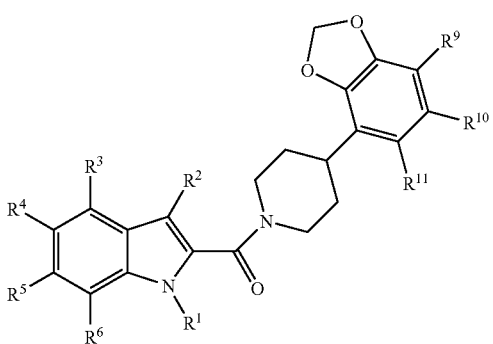

(I-a″)

wherein $R^1$ to $R^{11}$ are as defined herein above.

In a certain embodiment, A is (a), X is CH₂ and Y is CH₂, i.e. a compound of formula (I-a‴):

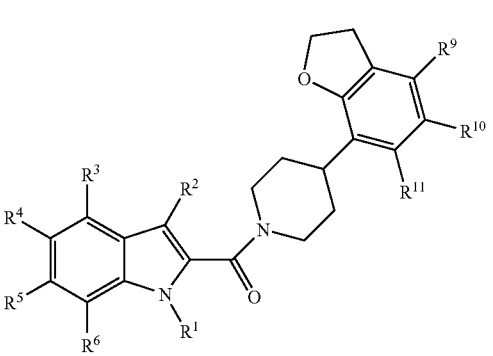

(I-a‴)

wherein $R^1$ to $R^{11}$ are as defined herein above.

In a further embodiment of the invention, A is (b); i.e. a compound of formula (I-b)

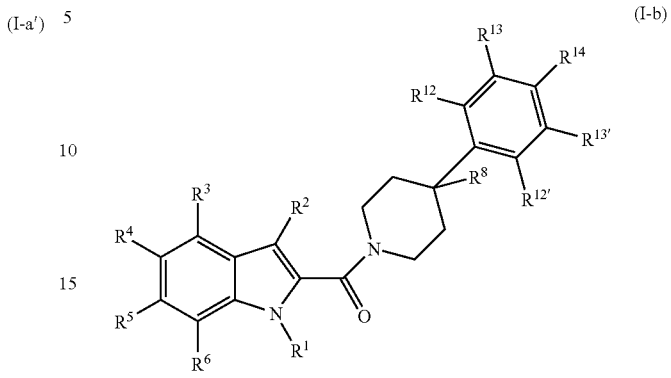

(I-b)

wherein $R^1$ to $R^{14}$ are as defined herein above.

A certain embodiment of the invention encompasses the compound of formula (I-b), wherein
$R^1$ is hydrogen,
  $C_{1-6}$-alkyl, optionally substituted by CN or OH, or
  —($C_{1-6}$-alkylene)-C(O)—NR$^a$R$^b$,
    wherein R$^a$ and R$^b$ are each independently hydrogen or $C_{1-6}$-alkyl;
$R^2$ is hydrogen, or $C_{1-6}$-alkyl;
$R^3$ is hydrogen, halo or $C_{1-6}$-alkyl;
$R^4$ is hydrogen,
  halo,
  $C_{1-6}$-alkyl,
  halo-$C_{1-6}$-alkyl,
  $C_{1-6}$-alkoxy, or
  halo-$C_{1-6}$-alkoxy;
$R^5$ is hydrogen, halo, $C_{1-6}$-alkyl, or $C_{1-6}$-alkoxy;
or $R^4$ and $R^5$ are bound together to form a ring with the benzo moiety, wherein
  —$R^4$—$R^5$— is —O—(CH₂)$_n$—O— wherein n is 1 or 2;
$R^6$ is hydrogen,
  $C_{1-6}$-alkyl, optionally substituted by CN or OH,
  —($C_{1-6}$-alkylene)-NR$^g$R$^h$
    wherein R$^g$ and R$^h$ are each independently selected from hydrogen and $C_{1-6}$-alkyl, or wherein
    R$^g$ and R$^h$ together with the nitrogen to which they are bound form a five or six membered heterocycle comprising one or two heteroatoms selected from the group consisting of nitrogen and oxygen,
  —($C_{1-6}$-alkylene)-C(O)—NR$^i$R$^j$
    wherein R$^i$ and R$^j$ are each independently
      hydrogen,
      $C_{1-6}$-alkyl, or
      —($C_{1-6}$-alkylene)-NR$^k$R$^l$,
        wherein R$^k$ and R$^l$ are each independently hydrogen or $C_{1-6}$-alkyl,
    or R$^i$ and R$^j$ together with the nitrogen to which they are bound form a five or six membered heterocycle comprising one or two heteroatoms selected from the group consisting of nitrogen and oxygen;
$R^8$ is hydrogen,
  $C_{1-6}$-alkoxy,
  CN,
  OH,
  COOR$^n$, or
  C(O)NR$^o$R$^p$;

$R^{12}$ and $R^{12'}$ are each independently hydrogen, $C_{1-6}$-alkoxy, $C_{1-6}$-alkyl, halo, halo-$C_{1-6}$-alkoxy, halo-$C_{1-6}$-alkyl, or nitro;

$R^{13}$, $R^{13'}$, and $R^{14}$ are each independently hydrogen, $C_{1-6}$-alkoxy, $C_{1-6}$-alkyl, halo, halo-$C_{1-6}$-alkoxy, or nitro.

Certain embodiments of the invention encompass compounds of formula (I-b) wherein $R^1$ is hydrogen,
  $C_{1-6}$-alkyl, optionally substituted by CN or OH, or
  —($C_{1-6}$-alkylene)-C(O)—NR$^a$R$^b$,
    wherein R$^a$ and R$^b$ are each independently hydrogen or $C_{1-6}$-alkyl;
$R^2$ is hydrogen, or $C_{1-6}$-alkyl;
$R^3$ is hydrogen;
$R^4$ is hydrogen or halo;
$R^5$ is hydrogen;
$R^6$ is hydrogen,
  $C_{1-6}$-alkyl, optionally substituted by CN or OH,
  —($C_{1-6}$-alkylene)-NR$^g$R$^h$
    wherein R$^g$ and R$^h$ are each independently selected from hydrogen and $C_{1-6}$-alkyl, or wherein
    R$^g$ and R$^h$ together with the nitrogen to which they are bound form a five or six membered heterocycle comprising one or two heteroatoms selected from the group consisting of nitrogen and oxygen;
$R^8$ is hydrogen or $C_{1-6}$-alkyl;
$R^{12}$, $R^{12'}$, $R^{13}$, $R^{13'}$, and $R^{14}$ are each independently hydrogen, $C_{1-6}$-alkoxy, $C_{1-6}$-alkyl, halo, halo-$C_{1-6}$-alkoxy, halo-$C_{1-6}$-alkyl, or nitro.

In a further embodiment of the invention,

A is (c); i.e. a compound of formula (I-c)

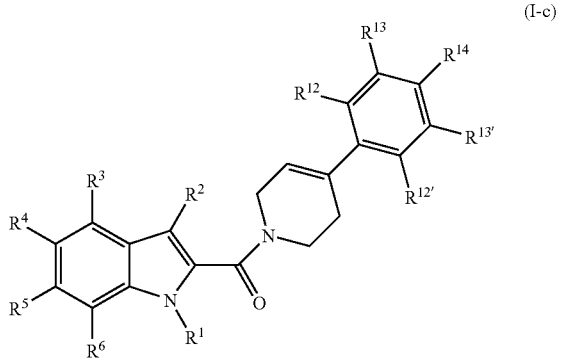

(I-c)

wherein $R^1$ to $R^{14}$ are as defined herein above.

A certain embodiment of the invention encompasses the compound of formula (I-c), wherein $R^1$ is hydrogen,
  $C_{1-6}$-alkyl, optionally substituted by CN or OH, or
  —($C_{1-6}$-alkylene)-C(O)—NR$^a$R$^b$,
    wherein R$^a$ and R$^b$ are each independently hydrogen or $C_{1-6}$-alkyl;
$R^2$ is hydrogen, or $C_{1-6}$-alkyl;
$R^3$ is hydrogen, halo or $C_{1-6}$-alkyl;
$R^4$ is hydrogen,
  halo,
  $C_{1-6}$-alkyl,
  halo-$C_{1-6}$-alkyl,
  $C_{1-6}$-alkoxy, or
  halo-$C_{1-6}$-alkoxy;
$R^5$ is hydrogen, halo, $C_{1-6}$-alkyl, or $C_{1-6}$-alkoxy;
or $R^4$ and $R^5$ are bound together to form a ring with the benzo moiety, wherein
  —$R^4$—$R^5$— is —O—(CH$_2$)$_n$—O— wherein n is 1 or 2;

$R^6$ is hydrogen,
  $C_{1-6}$-alkyl, optionally substituted by CN or OH,
  —($C_{1-6}$-alkylene)-NR$^g$R$^h$
    wherein R$^g$ and R$^h$ are each independently selected from hydrogen and $C_{1-6}$-alkyl, or wherein
    R$^g$ and R$^h$ together with the nitrogen to which they are bound form a five or six membered heterocycle comprising one or two heteroatoms selected from the group consisting of nitrogen and oxygen,
  —($C_{1-6}$-alkylene)-C(O)—NR$^i$R$^j$
    wherein R$^i$ and R$^j$ are each independently
      hydrogen,
      $C_{1-6}$-alkyl,
      —$C_{1-6}$-alkylene)-NR$^k$R$^l$,
        wherein R$^k$ and R$^l$ are each independently hydrogen or $C_{1-6}$-alkyl,
      or R$^i$ and R$^j$ together with the nitrogen to which they are bound form a five or six membered heterocycle comprising one or two heteroatoms selected from the group consisting of nitrogen and oxygen;
$R^8$ is hydrogen,
  $C_{1-6}$-alkoxy,
  CN,
  OH,
  COOR$^n$, or
  C(O)NR$^o$R$^p$;
$R^{12}$, $R^{12'}$, $R^{13}$, $R^{13'}$, and $R^{14}$ are each independently hydrogen, $C_{1-6}$-alkoxy, $C_{1-6}$-alkyl, halo, halo-$C_{1-6}$-alkoxy, halo-$C_{1-6}$-alkyl or nitro.

Preferred compounds of the invention are

{5-Chloro-2-[4-(2-oxo-2,3-dihydro-benzooxazol-7-yl)-piperidine-1-carbonyl]-1H-indol-7-yl}-acetonitrile, 7-[1-(5-Chloro-7-morpholin-4-ylmethyl-1H-indole-2-carbonyl)-piperidin-4-yl]-3H-benzooxazol-2-one, (5-Chloro-1H-indol-2-yl)-(4-methoxy-4-phenyl-piperidin-1-yl)-methanone, (5-Chloro-1H-indol-2-yl)-[4-(3-chloro-phenyl)-piperidin-1-yl]-methanone, (5-Chloro-1H-indol-2-yl)-[4-(2,6-dimethoxy-phenyl)-piperidin-1-yl]-methanone, 2-{5-Chloro-2-[4-(2,6-dimethoxy-phenyl)-piperidine-1-carbonyl]-indol-1-yl}-N,N-dimethyl-acetamide, {5-Chloro-2-[4-(2,6-dimethoxy-phenyl)-piperidine-1-carbonyl]-indol-1-yl}-acetonitrile, {2-[4-(2,6-Dimethoxy-phenyl)-piperidine-1-carbonyl]-1H-indol-7-yl}-acetonitrile, {5-Chloro-2-[4-(2,6-dimethoxy-phenyl)-piperidine-1-carbonyl]-1H-indol-7-yl}-acetonitrile, {5-Chloro-2-[4-(2-methoxy-phenyl)-piperidine-1-carbonyl]-1H-indol-7-yl}-acetonitrile, (5-Chloro-7-morpholin-4-ylmethyl-1H-indol-2-yl)-[4-(2-methoxy-phenyl)-piperidin-1-yl]-methanone, and (3,7-Dimethyl-1H-indol-2-yl)-(4-phenyl-3,6-dihydro-2H-pyridin-1-yl)-methanone.

The invention also encompasses methods for the treatment of dysmenorrhea, hypertension, chronic heart failure, inappropriate secretion of vasopressin, liver cirrhosis, nephrotic syndrome, obsessive compulsive disorder, anxiety and depressive disorders which comprises administering a therapeutically effect amount of a compound of formula (I), (Ia), (Ib), or (Ic).

The invention also encompasses a pharmaceutical composition comprising a compound of formula (I), (Ia), (Ib), or (Ic) and a pharmaceutically acceptable carrier. The pharmaceutical composition can further comprise at least one pharmaceutically acceptable excipient.

In a certain embodiment, the compound of the invention can be manufactured according to a process comprising reacting a compound of formula (II):

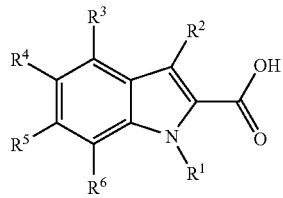

with an amine of the formula A-H wherein A and $R^1$ to $R^6$ are as defined above.

In another embodiment, the compounds of the invention can be manufactured according to a process comprising reacting a compound of formula (I-1):

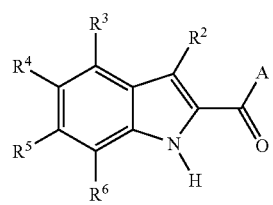

with an electophlie of formula $R^1$-hal, to give a compound of general formula (I) as defined herein above.

The synthesis of compounds of general formula (I) will be described in more detail below and in the examples.

General scheme A

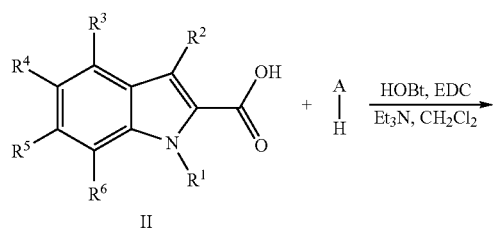

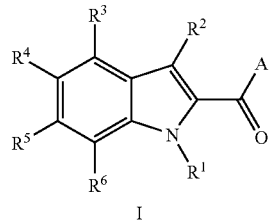

Compounds of formula (I) can be prepared via an amide coupling between an indole 2-carboxylic acid (II) and a compound of formula (A-H), wherein A is defined as hereinabove. The usual reagents and protocols known in the art can be used to effect the amide coupling. Indole 2-carboxylic acids (II) are either commercially available or readily prepared using procedures described hereinafter. The compounds of formula (A-H) are either commercially available or prepared using methods known in the art starting from commercially available materials. General scheme A is hereinafter further illustrated with general procedure I.

General scheme B

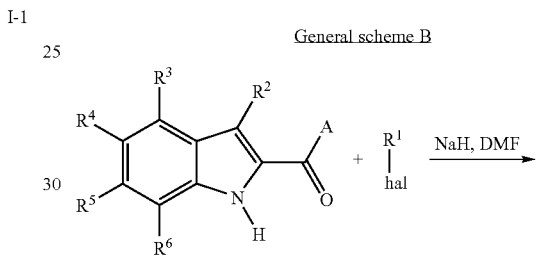

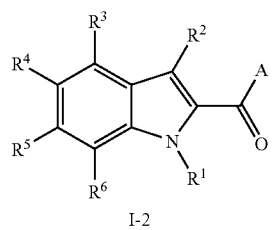

Compounds of formula (I-2) (compounds of formula (I) wherein $R^1$ is different from H), can be prepared by alkylation of the indole derivative of formula (I-1), with an electrophile of formula $R^1$-hal (commercially available, wherein hal is halo, preferably Cl or Br) using standard procedures. Derivatives (1-1) are prepared using the amide coupling as described in the general scheme A.

General scheme C: preparation of acids II

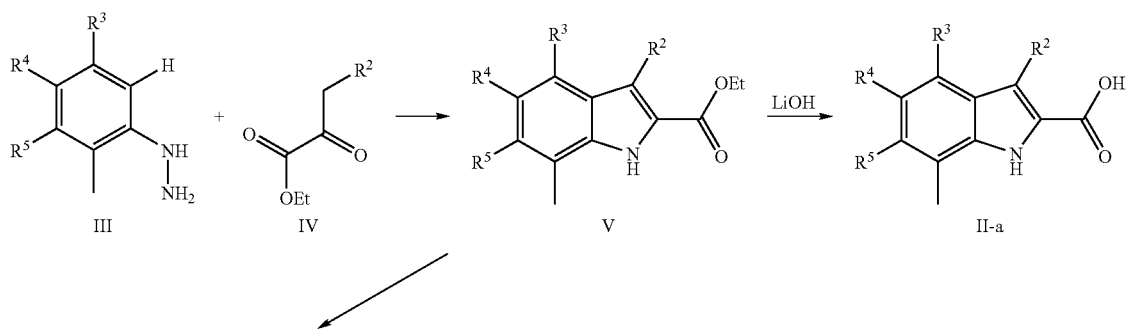

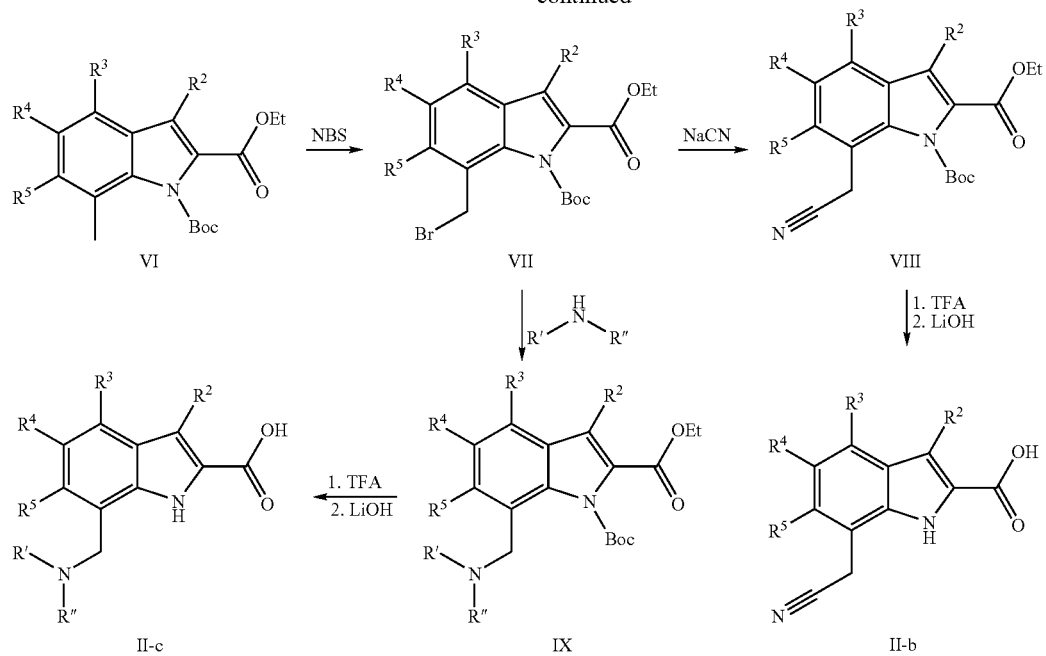

Substituted indole 2-carboxylic acids can be prepared according to the general scheme C. Indoles V are obtained by a Fischer indole synthesis from an aryl hydrazine III and a α-ketoester IV. Saponification gives an acid of formula II-a. Alternatively, Boc protection of the indole nitrogen gives VI. Selective bromination of the methyl group in the 7-position of the indole using NBS affords VII. Subsequent nucleophilic substitution of 7-bromomethyl indole intermediate VII with NaCN or a secondary amine yields intermediates VIII and IX, respectively. After N-deprotection and saponification of the ester moiety, the corresponding carboxylics acids II-b and II-c are obtained.

Abbreviations Used

NBS=N-Bromosuccinimide
Boc=tert-buthoxycarbonyl

The compounds of the present invention exhibit V1a activity, which may be detected as described below:

V1a Activity

Material & Method:

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells were resuspended in 30 ml freshly prepared ice cold Lysis buffer (50 mM HEPES, 1 mM EDTA, 10 mM $MgCl_2$ adjusted to pH=7.4+complete cocktail of protease inhibitor (Roche Diagnostics)), homogenized with Polytron for 1 min, and sonicated on ice for 2×2 minutes at 80% intensity (Vibracell sonicator). The preparation was centrifuged 20 min at 500 g at 4° C., the pellet was discarded and the supernatant centrifuged 1 hour at 43'000 g at 4° C. (19'000 rpm). The pellet was resuspended in 12.5 ml Lysis buffer+ 12.5 ml Sucrose 20% and homogenized using a Polytron for 1-2 min. The protein concentration was determined by the Bradford method and aliquots were stored at −80° C. until use. For binding studies 60 mg Yttrium silicate SPA beads (Amersham) were mixed with an aliquot of membrane in binding buffer (50 mM Tris, 120 mM NaCl, 5 mM KCl, 2 mM $CaCl_2$, 10 mM $MgCl_2$) for 15 minutes with mixing. 50 ul of bead/membrane mixture was then added to each well of a 96 well plate, followed by 50 ul of 4 nM 3H-Vasopressin (American Radiolabeled Chemicals). For total binding measurement 100 ul of binding buffer were added to the respective wells, for non-specific binding 100 ul of 8.4 mM cold vasopressin were added, and for compound testing 100 ul of a serial dilution of each compound in 2% DMSO were added. The plate was incubated 1 h at room temperature, centrifuged 1 min at 1000 g and counted on a Packard Top-Count. Non-specific binding counts were subtracted from each well and data was normalized to the maximum specific binding set at 100%. To calculate an IC 50 the curve was fitted using a non-linear regression model (XLfit) and the Ki was calculated using the Cheng-Prussoff equation.

| Example | pki (hV1a) |
|---|---|
| 1 | 7.89 |
| 2 | 8.185 |
| 5 | 7.39 |
| 6 | 7.3 |
| 7 | 7.855 |
| 8 | 7.065 |
| 9 | 7.71 |
| 10 | 7.34 |
| 11 | 7.265 |
| 12 | 7.015 |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula (I) should be appropriate, although the above upper limit can also be exceeded when necessary.

The following Examples illustrate the present invention without limiting it. All temperatures are given in degrees Celsius.

Example A

Tablets of the following composition can be manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition can be manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch can be firstly mixed in a mixer and then in a comminuting machine. The mixture then can be returned to the mixer, the talc can be added thereto and mixed thoroughly. The mixture can be filled by machine into hard gelatine capsules.

Example C

Suppositories of the following composition can be manufactured:

|  | mg/supp. |
| --- | --- |
| Active substance | 15 |
| Suppository mass | 1285 |
| Total | 1300 |

The suppository mass can be melted in a glass or steel vessel, mixed thoroughly and cooled to 45° C. Thereupon, the finely powdered active substance can be added thereto and stirred until it has dispersed completely. The mixture can be poured into suppository moulds of suitable size, left to cool; the suppositories then can be removed from the moulds and packed individually in wax paper or metal foil.

In the following, the synthesis of compounds of formula (I) is further exemplified: The compounds of formula I may be prepared in accordance with the process variants as described above. The starting materials described in the Example section are either commercially available or are otherwise known or derived from the chemical literature, for instance as cited below, or may be prepared as described in the Examples section.

Examples

General Procedure I

Amide Coupling

To a 0.1 M stirred solution of an indole-2-carboxylic acid derivative of type (II) in $CH_2Cl_2$ are added EDC (1.3 eq), HOBt (1.3 eq), $Et_3N$ (1.3 eq) and the amine derivative (A-H, as defined above, 1 eq). The mixture is stirred overnight at room temperature and then poured onto water and extracted with $CH_2Cl_2$. The combined organic phases are dried over $Na_2SO_4$ and concentrated in vacuo. Flash chromatography or preparative HPLC affords a compound of formula (I).

General Procedure II

Alkylation

To a 0.1 M stirred solution of a derivative of general formula (I-1) in DMF is added NaH (60% in oil, 2.1 eq.). After stirring the mixture at room temperature for 30 min. the electrophilic reactant $R^1$-hal (1.1 eq.) is added. The mixture is stirred an additional 14 hours at 60° C. and then poured onto water and extracted with ethyl acetate. The combined organic phases are dried over Na₂SO₄ and concentrated in vacuo. Purification by preparative HPLC affords the corresponding derivatives of general formula (I-2).

Preparation of Acids II

Acid 1: 5-Chloro-7-cyanomethyl-1H-indole-2-carboxylic acid

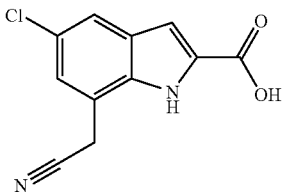

a) 2-[(4-Chloro-2-methyl-phenyl)-hydrazono]-prop ionic acid ethyl ester

To a stirred solution of 0.55 g (2.85 mmol) of (4-chloro-2-methyl-phenyl)-hydrazine, in acetic acid (5 ml), was added 0.34 g (2.91 mmol) of ethyl pyruvate. The mixture was stirred 2 hours at 35° C., poured onto an aqueous solution of sat. NaHCO₃ and then extracted with ethyl acetate. The combined organic phases were dried over Na₂SO₄ and concentrated in vacuo, to afford 0.702 g (97%) of 2-[(4-chloro-2-methyl-phenyl)-hydrazono]-propionic acid ethyl ester as a light orange solid.

b) 5-Chloro-7-methyl-1H-indole-2-carboxylic acid ethyl ester

To a solution of 0.70 g (2.75 mmol) of 2-[(4-chloro-2-methyl-phenyl)-hydrazono]-propionic acid ethyl ester in a sealed tube was added toluene (10 ml) and amberlyst 15 (1.60 g). The reaction mixture was heated at 120° C. over the night. The reaction mixture was concentrated under vacuo and purified by flash chromatography (SiO2, EtOAc/Hex 1/6) to afford 0.22 g (34%) of 5-chloro-7-methyl-1H-indole-2-carboxylic acid ethyl ester as a white solid. ES-MS m/e (%): 238.1 (M+H⁺).

c) 5-Chloro-7-methyl-indole-1,2-dicarboxylic acid 1-tert-butyl ester 2-ethyl ester To a solution of 0.22 g (0.9 mmol) of 5-chloro-7-methyl-1H-indole-2-carboxylic acid ethyl ester in CH₂Cl₂ (10 ml), 0.21 g of di-tert-butyl dicarbonate, 0.13 ml of Et₃N and 23 mg of DMAP were added. The reaction mixture was stirred at RT for 2 hours, poured onto an aqueous solution of HCl 1M and extracted with CH₂Cl₂. The reaction mixture was concentrated under vacuo and purified by flash chromatography (SiO2, EtOAc/Hex 1/9) to afford 0.30 g (97%) of 5-chloro-7-methyl-indole-1,2-dicarboxylic acid 1-tert-butyl ester 2-ethyl ester as a light yellow solid.

d) 7-Bromomethyl-5-chloro-indole-1,2-dicarboxylic acid 1-tert-butyl ester 2-ethyl ester To a solution of 0.30 g (0.9 mmol) of 5-chloro-7-methyl-indole-1,2-dicarboxylic acid 1-tert-butyl ester 2-ethyl ester in CCl₄ (10 ml), 016 g N-bromosuccinimide (NBS) and 11 mg of benzoyl peroxide were added. The reaction mixture was heated at reflux for one hour and cooled down to RT. The succinimide was filtered off and the solvent removed under reduced pressure to afford 0.35 g (95%) of 7-bromomethyl-5-chloro-indole-1,2-dicarboxylic acid 1-tert-butyl ester 2-ethyl ester as a light brown solid. This product was directly used in the next step (unstable).

e) 5-Chloro-7-cyanomethyl-indole-1,2-dicarboxylic acid 1-tert-butyl ester 2-ethyl ester To a solution of 1.00 g (2.4 mmol) of 7-bromomethyl-5-chloro-indole-1,2-dicarboxylic acid 1-tert-butyl ester 2-ethyl ester in DMSO (10 ml) at RT, 012 g of sodium cyanide was added. The reaction mixture was stirred at RT for one hour, poured on a saturated aqueous ammonium chloride solution and the product was extracted with EtOAc. The combined organic phases were dried over Na₂SO₄ and concentrated in vacuo. Flash chromatography (SiO₂, EtOAc/Hex 9/1) afforded 0.31 g (36%) of 5-chloro-7-cyanomethyl-indole-1, 2-dicarboxylic acid 1-tert-butyl ester 2-ethyl ester as a light yellow oil.

f) 5-Chloro-7-cyanomethyl-1H-indole-2-carboxylic acid ethyl ester

To a solution of 0.30 g (0.8 mmol) of 5-chloro-7-cyanomethyl-indole-1,2-dicarboxylic acid 1-tert-butyl ester 2-ethyl ester in CH₂Cl₂ (8 ml) at RT was added 2 ml of TFA. The reaction mixture was stirred at RT for one hour and concentrated under vacuo. The crude was taken up in EtOAc and neutralized with aqueous NaHCO₃. The combined organic phases were dried over Na₂SO₄ and concentrated in vacuo. Preparative HPLC (30% CH₃CN/H₂O) afforded 81 mg (35%) of 5-chloro-7-cyanomethyl-1H-indole-2-carboxylic acid ethyl ester as a white solid.

g) 5-Chloro-7-cyanomethyl-1H-indole-2-carboxylic acid

To a solution of 81 mg (0.3 mmol) of 5-chloro-7-cyanomethyl-1H-indole-2-carboxylic acid ethyl ester in THF/EtOH/H₂O (5 ml) at RT was added 39 mg of LiOH.H₂O. The reaction mixture was stirred at 40° C. for three hours and then acidified with aqueous HCl 1M. The product was extracted with EtOAc and concentrated under vacuo to afford 71 mg (98%) of 5-chloro-7-cyanomethyl-1H-indole-2-carboxylic acid as a white solid. ES-MS m/e (%): 232.9 (M−H⁺).

Acid 2: 5-Chloro-7-morpholin-4-ylmethyl-1H-indole-2-carboxylic acid

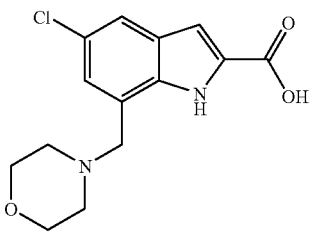

a) 5-Chloro-7-morpholin-4-ylmethyl-1H-indole-2-carboxylic acid ethyl ester

To a solution of 0.11 g (0.26 mmol) of 7-bromomethyl-5-chloro-indole-1,2-dicarboxylic acid 1-tert-butyl ester 2-ethyl ester in THF (1 ml) at RT, 40 μl of morpholine was added. The reaction mixture was stirred at 40° C. for one hour and concentrated under vacuo. The crude was dissolved in CH₂Cl₂ (1 m) and at RT, 0.2 ml of TFA was added and stirring was continued over night. Preparative HPLC (30% CH₃CN/H₂O) afforded 53 mg (62%) of 5-chloro-7-morpholin-4-ylmethyl-1H-indole-2-carboxylic acid ethyl ester as colorless oil.

b) 5-Chloro-7-morpholin-4-ylmethyl-1H-indole-2-carboxylic acid

To a solution of 53 mg (0.16 mmol) of 5-chloro-7-morpholin-4-ylmethyl-1H-indole-2-carboxylic acid ethyl ester in THF/EtOH/H₂O (2.5 ml) at RT was added 21 mg of LiOH.H₂O. The reaction mixture was stirred at 45° C. for one hour and then acidified with aqueous HCl 1M. The product was extracted with EtOAc and concentrated under vacuo to afford 12 mg (25%) of 5-chloro-7-morpholin-4-ylmethyl-1H-indole-2-carboxylic acid as a white solid. ES-MS m/e (%): 293.1 (M−H$^+$).

Acid 3: 7-Cyanomethyl-1H-indole-2-carboxylic acid

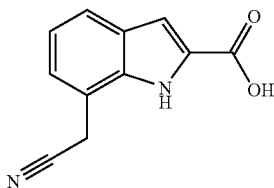

To a solution of 100 mg (0.46 mmol) of 7-cyanomethyl-1H-indole-2-carboxylic acid ethyl ester (the preparation of which is described in Chem. Pharm. Bull. 1996, 44, 55) in THF/EtOH/H₂O (5 ml) at RT was added 50 mg of LiOH.H₂O. The reaction mixture was stirred at 45° C. for one hour and then acidified with aqueous HCl 1M. The product was extracted with EtOAc and concentrated under vacuo to afford 80 mg (85%) of 7-Cyanomethyl-1H-indole-2-carboxylic acid as a white solid. ES-MS m/e (%): 199.6 (M−H$^+$).

Acid 4: 3,7-Dimethyl-1H-indole-2-carboxylic acid

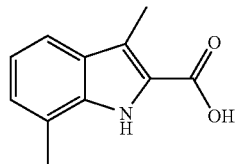

The title compound is prepared by saponification of 3,7-dimethyl-1H-indole-2-carboxylic acid ethyl ester (prepared by Fischer indole synthesis as described in Tetrahedron Lett. 2003, 44, 5665) using the procedure described above for the synthesis of 5-chloro-7-cyanomethyl-1H-indole-2-carboxylic acid (acid 1, step g)).

Examples

Example 1

{5-Chloro-2-[4-(2-oxo-2,3-dihydro-benzooxazol-7-yl)-piperidine-1-carbonyl]-1H-indol-7-yl}-acetonitrile

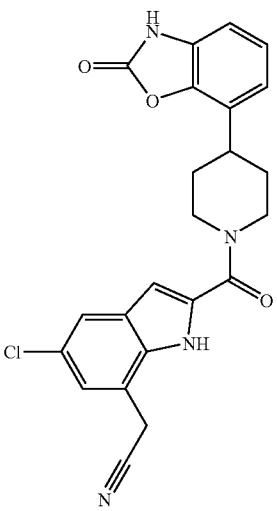

Amide coupling according to general procedure I:
Amine: 7-piperidin-4-yl-3H-benzooxazol-2-one (described in WO01/85725),
Acid: 5-Chloro-7-cyanomethyl-1H-indole-2-carboxylic acid,
ES-MS m/e (%): 435.1 (M+H$^+$).

Example 2

7-[1-(5-Chloro-7-morpholin-4-ylmethyl-1H-indole-2-carbonyl)-piperidin-4-yl]-3H-benzooxazol-2-one

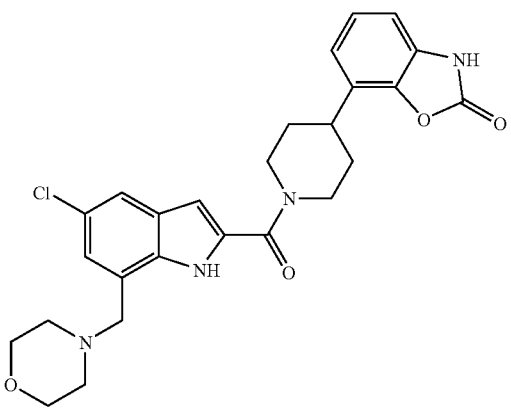

Amide coupling according to general procedure I:
Amine: 7-piperidin-4-yl-3H-benzooxazol-2-one (described in WO01/85725),
Acid: 5-Chloro-7-morpholin-4-ylmethyl-1H-indole-2-carboxylic acid
ES-MS m/e (%): 495.1 (M+H$^+$).

Example 3

(5-Chloro-1H-indol-2-yl)-(4-methoxy-4-phenyl-piperidin-1-yl)-methanone

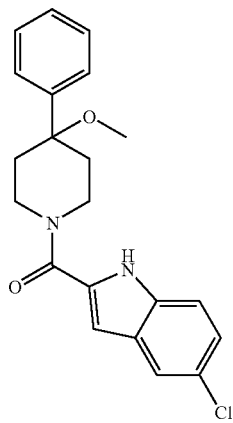

Amide coupling according to general procedure I:
Amine: 4-Methoxy-4-phenyl-piperidine (described in WO 2004035549),
Acid: 5-Chloro-1H-indole-2-carboxylic acid,
ES-MS m/e (%): 369.4 (M+H$^+$).

Example 4

(5-Chloro-1H-indol-2-yl)-[4-(3-chloro-phenyl)-piperidin-1-yl]-methanone

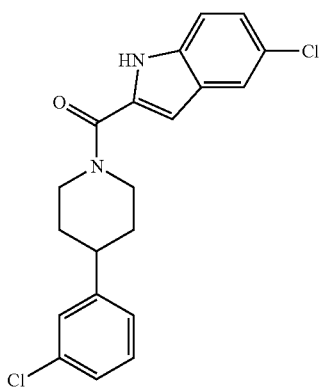

Amide coupling according to general procedure I:
Amine: 4-(3-Chloro-phenyl)-piperidine,
Acid: 5-Chloro-1H-indole-2-carboxylic acid,
ES-MS m/e (%): 373.3 (M+H$^+$).

Example 5

(5-Chloro-1H-indol-2-yl)-[4-(2,6-dimethoxy-phenyl)-piperidin-1-yl]-methanone

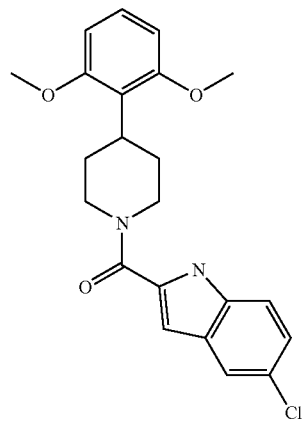

Amide coupling according to general procedure I:
Amine: 4-(2,6-Dimethoxy-phenyl)-piperidine (described in WO2000/014067),
Acid: 5-Chloro-1H-indole-2-carboxylic acid,
ES-MS m/e (%): 399.2 (M+H$^+$).

Example 6

2-{5-Chloro-2-[4-(2,6-dimethoxy-phenyl)-piperidine-1-carbonyl]-indol-1-yl}-N,N-dimethyl-acetamide

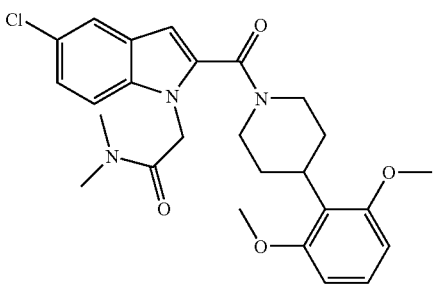

To a stirred solution of 40 mg (0.10 mmol) of (5-chloro-1H-indol-2-yl)-[4-(2,6-dimethoxy-phenyl)-piperidin-1-yl]-methanone in DMF (3 ml) at RT was added 5 mg (0.11 mmol) of NaH (in oil, 55%). After 20 minutes, 12 mg (0.10 mmol) of 2-chloro-N,N-dimethyl-acetamide was added and stirring was continued over night. The reaction mixture was concentrated in vacuo and purification by preparative HPLC (30% CH$_3$CN/H$_2$O) afforded 35 mg (72%) of 2-{5-chloro-2-[4-(2,6-dimethoxy-phenyl)-piperidine-1-carbonyl]-indol-1-yl}-N,N-dimethyl-acetamide as a white solid.
ES-MS m/e (%): 484.3 (M+H$^+$).

Example 7

{5-Chloro-2-[4-(2,6-dimethoxy-phenyl)-piperidine-1-carbonyl]-indol-1-yl}-acetonitrile

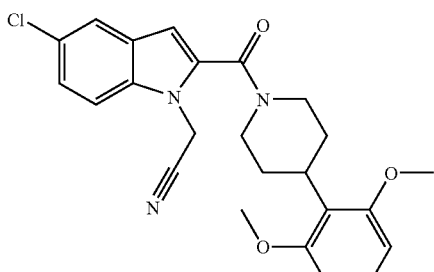

To a stirred solution of 40 mg (0.10 mmol) of (5-chloro-1H-indol-2-yl)-[4-(2,6-dimethoxy-phenyl)-piperidin-1-yl]-methanone in DMF (3 ml) at RT was added 5 mg (0.11 mmol) of NaH (in oil, 55%). After 20 minutes, 8 mg (0.10 mmol) of chloro-acetonitrile was added and stirring was continued over night. The reaction mixture was concentrated in vacuo and purification by preparative HPLC (30% CH$_3$CN/H$_2$O) afforded 9 mg (18%) of {5-chloro-2-[4-(2,6-dimethoxy-phenyl)-piperidine-1-carbonyl]-indol-1-yl}-acetonitrile as a white solid.

ES-MS m/e (%): 438.1 (M+H$^+$).

Example 8

{2-[4-(2,6-Dimethoxy-phenyl)-piperidine-1-carbonyl]-1H-indol-7-yl}-acetonitrile

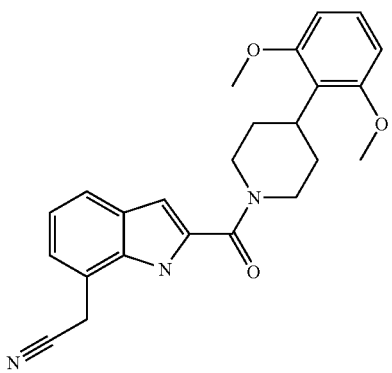

Amide coupling according to general procedure I:
Amine: 4-(2,6-Dimethoxy-phenyl)-piperidine (described in WO2000014067),
Acid: 7-Cyanomethyl-1H-indole-2-carboxylic acid,
ES-MS m/e (%): 404.4 (M+H$^+$).

Example 9

{5-Chloro-2-[4-(2,6-dimethoxy-phenyl)-piperidine-1-carbonyl]-1H-indol-7-yl}-acetonitrile

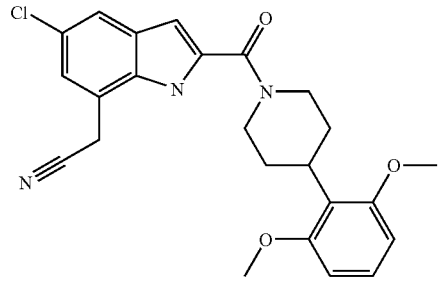

Amide coupling according to general procedure I:
Amine: 4-(2,6-Dimethoxy-phenyl)-piperidine (described in WO2000014067),
Acid: 5-Chloro-7-cyanomethyl-1H-indole-2-carboxylic acid,
ES-MS m/e (%): 438.1 (M+H$^+$).

Example 10

{5-Chloro-2-[4-(2-methoxy-phenyl)-piperidine-1-carbonyl]-1H-indol-7-yl}-acetonitrile

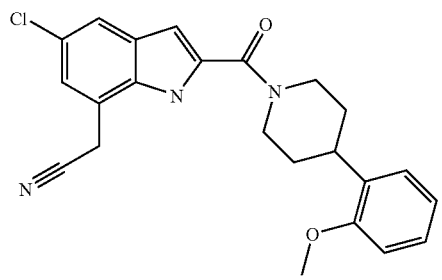

Amide coupling according to general procedure I:
Amine: 4-(2-Methoxy-phenyl)-piperidine,
Acid: 5-Chloro-7-cyanomethyl-1H-indole-2-carboxylic acid,
ES-MS m/e (%): 408.3 (M+H$^+$).

Example 11

(5-Chloro-7-morpholin-4-ylmethyl-1H-indol-2-yl)-[4-(2-methoxy-phenyl)-piperidin-1-yl]-methanone

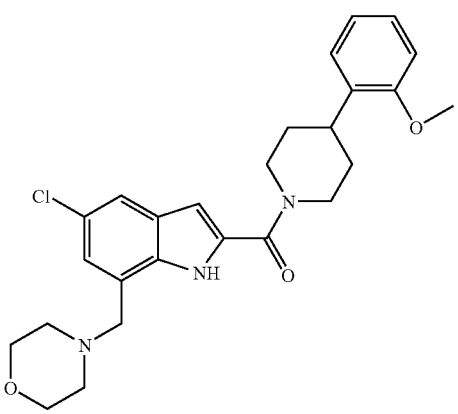

Amide coupling according to general procedure I:
Amine: 4-(2-Methoxy-phenyl)-piperidine,
Acid: 5-Chloro-7-morpholin-4-ylmethyl-1H-indole-2-carboxylic acid
(ES-MS m/e (%): 468.4 (M+H$^+$).

Example 12

(3,7-Dimethyl-1H-indol-2-yl)-(4-phenyl-3,6-dihydro-2H-pyridin-1-yl)-methanone

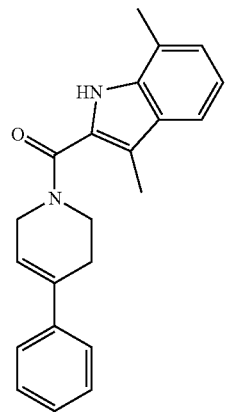

Amide coupling according to general procedure I:
Amine: 4-Phenyl-1,2,3,6-tetrahydro-pyridine,
Acid: 3,7-Dimethyl-1H-indole-2-carboxylic acid,
ES-MS m/e (%): 331.4 (M+H$^+$).

The invention claimed is:
1. The compound of the formula (Ia)

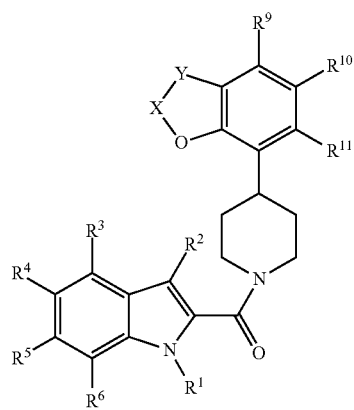

(Ia)

wherein
X is C=O and Y is NR$^7$, or
X is CH$_2$ and Y is O, or
X is CH$_2$ and Y is CH$_2$,
R$^1$ is hydrogen,
  C$_{1-6}$-alkyl, optionally substituted by CN or OH, or
  —(C$_{1-6}$-alkylene)-C(O)—NR$^a$R$^b$;
R$^2$ is hydrogen,
  C$_{1-6}$-alkyl,
  C$_{1-6}$-alkoxy,
  —(C$_{1-6}$-alkylene)-NR$^c$R$^d$,
  —(C$_{1-6}$-alkylene)-C(O)R$^f$,
  benzyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano, or
  phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano;
R$^3$ is hydrogen,
  halo, or
  C$_{1-6}$-alkyl;
R$^4$ is hydrogen,
  halo,
  C$_{1-6}$-alkyl,
  halo-C$_{1-6}$-alkyl,
  C$_{1-6}$-alkoxy,
  halo-C$_{1-6}$-alkoxy, or
  —O—C$_{2-10}$-alkenyl;
R$^5$ is hydrogen,
  halo,
  C$_{1-6}$-alkyl, or
  C$_{1-6}$-alkoxy;
R$^6$ is hydrogen,
  C$_{1-6}$-alkyl, optionally substituted by CN or OH,
  —(C$_{1-6}$-alkylene)-NR$^g$R$^h$
  —(C$_{1-6}$-alkylene)-C(O)—NR$^i$R$^j$
  —O-benzyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano,
  nitro,
  halo,
  cyano,
  C$_{1-6}$-alkoxy,
  halo-C$_{1-6}$-alkoxy,
  halo-C$_{1-6}$-alkyl,
  —(C$_{1-6}$-alkylene)-C(O)R$^f$,
  phenyl, or 5 to 6-membered heteroaryl, optionally substituted by halo, halo-C$_{1-6}$-alkyl, C$_{1-6}$-alkyl, C$_{1-6}$-alkoxy, halo-C$_{1-6}$-alkoxy, nitro, or cyano,
  —(C$_{1-3}$-alkylene)-R$^m$, wherein R$^m$ is phenyl, a 5- to 6-membered heteroaryl, 4- to 6-membered heterocycloalkyl or 3 to 6-membered cycloalkyl,
  each optionally substituted by one or more halo, halo-C$_{1-6}$-alkyl, C$_{1-6}$-alkyl, C$_{1-6}$-alkoxy, halo-C$_{1-6}$-alkoxy, nitro, or cyano;
R$^7$ is hydrogen or C$_{1-6}$-alkyl;
R$^9$, R$^{10}$, and R$^{11}$ are each independently hydrogen, halo, C$_{1-6}$-alkyl, halo-C$_{1-6}$-alkyl, C$_{1-6}$-alkoxy or halo-C$_{1-6}$-alkoxy;
R$^a$, R$^b$, R$^i$ and R$^j$ are each independently
  hydrogen,
  C$_{1-6}$-alkyl,
  —(C$_{1-6}$-alkylene)-NR$^k$R$^l$,
    wherein R$^k$ and R$^l$ are each independently hydrogen or C$_{1-6}$-alkyl, or
  R$^a$ and R$^b$, or R$^i$ and R$^j$ together with the nitrogen to which they are bound form a five or six membered heterocycle comprising one or two heteroatoms selected from the group consisting of nitrogen, oxygen and sulfur;
R$^c$, R$^d$, R$^g$ and R$^h$ are each independently
  hydrogen,
  C$_{1-6}$-alkyl,
  —C(O)R$^e$, or —S(O)$_2$R$^e$, wherein $R^e$ is selected from
- hydrogen,
- $C_{1-6}$-alkyl, or
- phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or $R^c$ and $R^d$, or $R^g$ and $R^h$ together with the nitrogen to which they are bound form a five or six membered heterocycle comprising one or two heteroatoms selected from the group consisting of nitrogen, oxygen and sulfur, or $R^c$ and $R^d$, or $R^g$ and $R^h$ together with the nitrogen to which they are bound form isoindole-1,3-dione;

$R^f$ is selected from the group consisting of
- hydrogen,
- $C_{1-6}$-alkyl,
- $C_{1-6}$-alkoxy, or
- phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;

$R^n$, $R^o$ and $R^p$ are each independently selected from the group consisting of hydrogen and $C_{1-6}$-alkyl, or a pharmaceutically acceptable salt thereof.

2. The compound of claim 1, wherein $R^a$ and $R^b$, $R^c$ and $R^d$, $R^i$ and $R^j$, or $R^g$ and $R^h$ together with the nitrogen atom to which they are attached form piperazine, 4-($C_{1-6}$-alkyl)-piperazine, 4-methylpiperazine, morpholine, piperidine, or pyrrolidine.

3. The compound of claim 1 wherein $R^m$ is a 5- to 6-membered heteroaryl selected from the group consisting of pyridine, pyrimidine, pyrazine, pyridazine, imidazole, pyrazole, oxazole, and isoxazole.

4. The compound of claim 1 wherein $R^m$ is a 4- to 6-membered heterocycloalkyl selected from the group consisting of pyrrolidine, oxethane, tetrahydropyrane, piperidine, morpholine, and piperazine.

5. The compound of claim 1, wherein $R^1$, $R^2$, $R^3$, $R^4$, $R^5$, and $R^6$ are not all hydrogen.

6. The compound of claim 1, wherein
$R^1$ is hydrogen,
- $C_{1-6}$-alkyl, optionally substituted by CN or OH, or
- ($C_{1-6}$-alkylene)-C(O)—NR$^a$R$^b$,
  wherein $R^a$ and $R^b$ are each independently hydrogen or $C_{1-6}$-alkyl.

7. The compound of claim 1, wherein
$R^2$ is hydrogen,
- $C_{1-6}$-alkyl,
- $C_{1-6}$-alkoxy,
- —($C_{1-6}$-alkylene)-NR$^c$R$^d$,
  wherein $R^c$ and $R^d$ are each independently
  - hydrogen,
  - —C(O)R$^e$, or —S(O)$_2$R$^e$
  wherein $R^e$ is selected from
  - hydrogen,
  - $C_{1-6}$-alkyl, and
  - phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or
  $R^c$ and $R^d$ together with the nitrogen to which they are bound form isoindole-1,3-dione,
- —($C_{1-6}$-alkylene)-C(O)R$^f$,
  wherein $R^f$ is selected from
  - hydrogen,
  - $C_{1-6}$-alkyl,
  - $C_{1-6}$-alkoxy, or
  - phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
  benzyl, optionally substituted by halo, halo-$C_{1-6}$-alkyl, $C_{1-6}$-alkyl, $C_{1-6}$-alkoxy, halo-$C_{1-6}$-alkoxy, nitro, or cyano, or
  phenyl, optionally substituted by halo, halo-$C_{1-6}$-alkyl, $C_{1-6}$-alkyl, $C_{1-6}$-alkoxy, halo-$C_{1-6}$-alkoxy, nitro, or cyano.

8. The compound of claim 1, wherein $R^2$ is hydrogen or $C_{1-6}$-alkyl.

9. The compound of claim 1, wherein $R^3$ is hydrogen.

10. The compound of claim 1, wherein $R^4$ is hydrogen, halo, $C_{1-6}$-alkyl, halo-$C_{1-6}$-alkyl or $C_{1-6}$-alkoxy.

11. The compound of claim 1, wherein
$R^6$ is hydrogen,
- $C_{1-6}$-alkyl, optionally substituted by CN or OH,
- —($C_{1-6}$-alkylene)-NR$^g$R$^h$
  wherein $R^g$ and $R^h$ are each independently selected from hydrogen and $C_{1-6}$-alkyl, or wherein
  $R^g$ and $R^h$ together with the nitrogen to which they are bound form a five or six membered heterocycle comprising one or two heteroatoms selected from the group of nitrogen, oxygen and sulfur,
- —($C_{1-6}$-alkylene)-C(O)—NR$^i$R$^j$
  wherein $R^i$ and $R^j$ are each independently
  - hydrogen,
  - $C_{1-6}$-alkyl,
  - —($C_{1-6}$-alkylene)-NR$^k$R$^l$,
  wherein $R^k$ and $R^l$ are each independently hydrogen or $C_{1-6}$-alkyl,
  or $R^i$ and $R^j$ together with the nitrogen to which they are bound form a five or six membered heterocycle comprising one or two heteroatoms selected from the group of nitrogen, oxygen and sulfur,
- —O-benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
- nitro,
- halo,
- cyano,
- $C_{1-6}$-alkoxy,
- halo-$C_{1-6}$-alkoxy,
- halo-$C_{1-6}$-alkyl,
- —($C_{1-6}$-alkylene)-C(O)R$^f$,
  $R^f$ is selected from
  - hydrogen,
  - $C_{1-6}$-alkyl,
  - $C_{1-6}$-alkoxy, or
  - phenyl or 5- to 6-membered heteroaryl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
- phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, —($C_{1-3}$-alkylene)-R$^m$, wherein $R^m$ is phenyl, a 5- to 6-membered heteroaryl, 4- to 6-membered heterocycloalkyl or 3 to 6-membered cycloalkyl,
  each optionally substituted by one or more halo, halo-$C_{1-6}$-alkyl, $C_{1-6}$-alkyl, $C_{1-6}$-alkoxy, halo-$C_{1-6}$-alkoxy, nitro, or cyano.

12. The compound of claim 1, wherein
R⁶ is hydrogen,
C$_{1-6}$-alkyl, optionally substituted by CN or OH,
—(C$_{1-6}$-alkylene)-NR$^g$R$^h$
wherein R$^g$ and R$^h$ are each independently selected from hydrogen and C$_{1-6}$-alkyl, or wherein
R$^g$ and R$^h$ together with the nitrogen to which they are bound form a five or six membered heterocycle comprising one or two heteroatoms selected from the group consisting of nitrogen and oxygen,
(C$_{1-6}$-alkylene)-C(O)—NR$^i$R$^j$
wherein R$^i$ and R$^j$ are each independently hydrogen,
C$_{1-6}$-alkyl, or
—(C$_{1-6}$-alkylene)-NR$^k$R$^l$,
wherein R$^k$ and R$^l$ are each independently hydrogen or C$_{1-6}$-alkyl,
or R$^i$ and R$^j$ together with the nitrogen to which they are bound form a five or six membered heterocycle comprising one or two heteroatoms selected from the group of nitrogen and oxygen
—(C$_{1-3}$-alkylene)-R$^m$, wherein
R$^m$ is phenyl, a 5- to 6-membered heteroaryl, 4- to 6-membered heterocycloalkyl or 3 to 6-membered cycloalkyl,
each optionally substituted by one or more halo, halo-C$_{1-6}$-alkyl, C$_{1-6}$-alkyl, C$_{1-6}$-alkoxy, halo-C$_{1-6}$-alkoxy, nitro, or cyano.

13. The compound of claim 1, wherein
X is C=O and Y is NR';
R¹ is hydrogen,
C$_{1-6}$-alkyl, optionally substituted by CN or OH, or
—(C$_{1-6}$-alkylene)-C(O)—NR$^a$R$^b$,
wherein R$^a$ and R$^b$ are each independently hydrogen or C$_{1-6}$-alkyl;
R² is hydrogen, or C$_{1-6}$-alkyl;
R³ is hydrogen, halo or C$_{1-6}$-alkyl;
R⁴ is hydrogen,
halo,
C$_{1-6}$-alkyl,
halo-C$_{1-6}$-alkyl,
C$_{1-6}$-alkoxy, or
halo-C$_{1-6}$-alkoxy;
R⁵ is hydrogen,
halo,
C$_{1-6}$-alkyl, or
C$_{1-6}$-alkoxy;
R⁶ is hydrogen,
C$_{1-6}$-alkyl, optionally substituted by CN or OH,
—(C$_{1-6}$-alkylene)-NR$^g$R$^h$
wherein R$^g$ and R$^h$ are each independently selected from hydrogen and C$_{1-6}$-alkyl, or wherein
R$^g$ and R$^h$ together with the nitrogen to which they are bound form a five or six membered heterocycle comprising one or two heteroatoms selected from the group of nitrogen and oxygen,
—(C$_{1-6}$-alkylene)-C(O)—NR$^i$R$^j$
wherein R$^k$ and R$^l$ are each independently hydrogen,
C$_{1-6}$-alkyl,
—(C$_{1-6}$-alkylene)-NR$^k$R$^l$,
wherein R$^k$ and R$^l$ are each independently hydrogen or C$_{1-6}$-alkyl,
or R$^i$ and R$^j$ together with the nitrogen to which they are bound form a five or six membered heterocycle comprising one or two heteroatoms selected from the group of nitrogen and oxygen;
R⁷ is hydrogen or C$_{1-6}$-alkyl;
R⁹, R¹⁰, and R¹¹ are each independently hydrogen, halo, C$_{1-6}$-alkyl, halo-C$_{1-6}$-alkyl, C$_{1-6}$-alkoxy or halo-C$_{1-6}$-alkoxy.

14. The compound of claim 1, selected from the group consisting of
{5-Chloro-2-[4-(2-oxo-2,3-dihydro-benzooxazol-7-yl)-piperidine-1-carbonyl]-1H-indol-7-yl}-acetonitrile, and
7-[1-(5-Chloro-7-morpholin-4-ylmethyl-1H-indole-2-carbonyl)-piperidin-4-yl]-3H-benzooxazol-2-one.

15. The compound of claim 1, having formula (I-a')

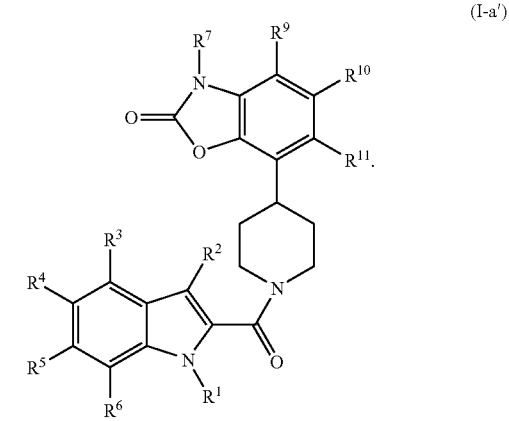

16. The compound of claim 1, having formula (I-a")

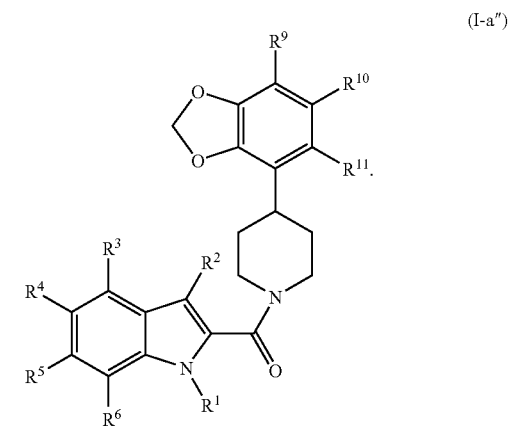

17. The compound of claim 1, having formula (I-a'")

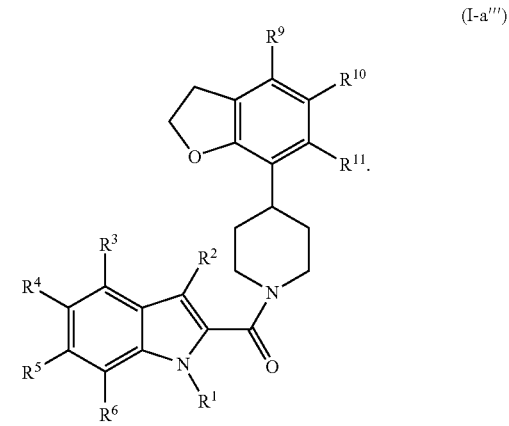

18. A pharmaceutical composition comprising a therapeutically effective amount of a compound of formula (Ia)

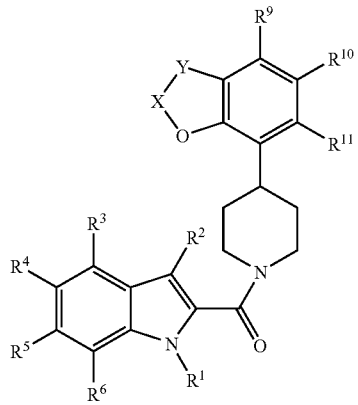

(Ia)

wherein
X is C=O and Y is NR$^7$, or
X is CH$_2$ and Y is O, or
X is CH$_2$ and Y is CH$_2$,
R$^1$ is hydrogen,
 C$_{1-6}$-alkyl, optionally substituted by CN or OH, or
 —(C$_{1-6}$-alkylene)-C(O)—NR$^a$R$^b$;
R$^2$ is hydrogen,
 C$_{1-6}$-alkyl,
 C$_{1-6}$-alkoxy,
 —(C$_{1-6}$-alkylene)-NR$^c$R$^d$,
 —(C$_{1-6}$-alkylene)-C(O)R$^f$,
 benzyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano, or
 phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano;
R$^3$ is hydrogen,
 halo, or
 C$_{1-6}$-alkyl;
R$^4$ is hydrogen,
 halo,
 C$_{1-6}$-alkyl,
 halo-C$_{1-6}$-alkyl,
 C$_{1-6}$-alkoxy,
 halo-C$_{1-6}$-alkoxy, or
 —O—C$_{2-10}$-alkenyl;
R$^5$ is hydrogen,
 halo,
 C$_{1-6}$-alkyl, or
 C$_{1-6}$-alkoxy;
R$^6$ is hydrogen,
 C$_{1-6}$-alkyl, optionally substituted by CN or OH,
 —(C$_{1-6}$-alkylene)-NR$^g$R$^h$
 —(C$_{1-6}$-alkylene)-C(O)—NR$^i$R$^j$
 —O-benzyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano,
 nitro,
 halo,
 cyano,
 C$_{1-6}$-alkoxy,
 halo-C$_{1-6}$-alkoxy,
 —(C$_{1-6}$-alkylene)-C(O)R$^f$,
 phenyl, or 5 to 6-membered heteroaryl, optionally substituted by halo, halo-C$_{1-6}$-alkyl, C$_{1-6}$-alkyl, C$_{1-6}$-alkoxy, halo-C$_{1-6}$-alkoxy, nitro, or cyano,
 —(C$_{1-3}$-alkylene)-R$^m$, wherein R$^m$ is phenyl, a 5- to 6-membered heteroaryl, 4- to 6-membered heterocycloalkyl or 3 to 6-membered cycloalkyl,
  each optionally substituted by one or more halo, halo-C$_{1-6}$-alkyl, C$_{1-6}$-alkoxy, halo-C$_{1-6}$-alkoxy, nitro, or cyano;
R$^7$ is hydrogen or C$_{1-6}$-alkyl;
R$^9$, R$^{10}$, and R$^{11}$ are each independently hydrogen, halo, C$_{1-6}$-alkyl, C$_{1-6}$-alkoxy or halo-C$_{1-6}$-alkoxy;
R$^a$, R$^b$, R$^i$ and R$^j$ are each independently
 hydrogen,
 C$_{1-6}$-alkyl,
 —(C$_{1-6}$-alkylene)-NR$^k$R$^l$,
  wherein R$^k$ and R$^l$ are each independently hydrogen or C$_{1-6}$-alkyl,
 or
 R$^a$ and R$^b$, or R$^i$ and R$^j$ together with the nitrogen to which they are bound form a five or six membered heterocycle comprising one or two heteroatoms selected from the group consisting of nitrogen, oxygen and sulfur;
R$^c$, R$^d$, R$^g$ and R$^h$ are each independently
 hydrogen,
 C$_{1-6}$-alkyl,
 —C(O)R$^e$, or —S(O)$_2$R$^e$,
  wherein R$^e$ is selected from
   hydrogen,
   C$_{1-6}$-alkyl, or
   phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano, or
 R$^c$ and R$^d$, or R$^g$ and R$^h$ together with the nitrogen to which they are bound form a five or six membered heterocycle comprising one or two heteroatoms selected from the group consisting of nitrogen, oxygen and sulfur, or
 R$^c$ and R$^d$, or R$^g$ and R$^h$ together with the nitrogen to which they are bound form isoindole-1,3-dione;
R$^f$ is selected from the group consisting of
 hydrogen,
 C$_{1-6}$-alkyl,
 C$_{1-6}$-alkoxy, or
 phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano;
R$^n$, R$^o$ and R$^p$ are each independently selected from the group consisting of selected from the group consisting of hydrogen and C$_{1-6}$-alkyl,
or a pharmaceutically acceptable salt thereof and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,076,360 B2 | Page 1 of 1 |
| APPLICATION NO. | : 11/947851 | |
| DATED | : December 13, 2011 | |
| INVENTOR(S) | : Bissantz et al. | |

It is certified that error appears in the above-identified patent and that said Letters Patent is hereby corrected as shown below:

ON THE TITLE PAGE:

Item (73) Assignee: Reads "Hoffman-La Roche Inc., Nutley, NJ (US)"
should read -- Hoffmann-La Roche Inc., Nutley, NJ (US) --.

Signed and Sealed this
Twenty-first Day of February, 2012

David J. Kappos
*Director of the United States Patent and Trademark Office*